(12) United States Patent
Manage

(10) Patent No.: US 9,957,559 B2
(45) Date of Patent: May 1, 2018

(54) SOLID GEL AMPLIFICATION METHOD AND APPARATUS FOR PLATFORM MOLECULAR DIAGNOSTICS

(71) Applicant: Damikka Manage, Edmonton (CA)

(72) Inventor: Damikka Manage, Edmonton (CA)

(73) Assignee: The Governors of the University of Alberta, Edmonton, Alberta ( * ) Notice: Subject to any disclaimer, the term of this patent is extended or adjusted under 35 U.S.C. 154(b) by 256 days.

(21) Appl. No.: 14/399,637

(22) PCT Filed: Feb. 25, 2013

(86) PCT No.: PCT/CA2013/000162
§ 371 (c)(1),
(2) Date: Nov. 7, 2014

(87) PCT Pub. No.: WO2013/166581
PCT Pub. Date: Nov. 14, 2013

(65) Prior Publication Data
US 2015/0240289 A1    Aug. 27, 2015

Related U.S. Application Data

(60) Provisional application No. 61/644,593, filed on May 9, 2012, provisional application No. 61/697,194, filed on Sep. 5, 2012.

(51) Int. Cl.
*C12Q 1/68* (2018.01)
*B01L 7/00* (2006.01)
(Continued)

(52) U.S. Cl.
CPC .......... *C12Q 1/686* (2013.01); *B01L 3/50851* (2013.01); *B01L 3/502707* (2013.01); *B01L 7/52* (2013.01); *B01L 9/065* (2013.01); *C12M 21/18* (2013.01); *C12M 23/16* (2013.01); *C12M 23/20* (2013.01); *C12M 43/00* (2013.01); *B01L 2200/0673* (2013.01); *B01L 2200/0689* (2013.01); *B01L 2300/069* (2013.01); *B01L 2300/0816* (2013.01);
(Continued)

(58) Field of Classification Search
CPC .............. A61B 5/00; G01N 27/44747; G01N 27/44782; G01N 27/44791; C12Q 1/686; B01L 3/5027; B01L 2200/12; B01L 3/502707; B81C 1/00119; B81C 99/009
See application file for complete search history.

(56) References Cited

U.S. PATENT DOCUMENTS

2002/0188221 A1* 12/2002 Sohrab ............... A61B 5/14865
600/573

OTHER PUBLICATIONS

Kaigala et al.(Lab Chip, 2007, 7, 384-387).*
Kaigala et al.(Lab Chip, 2007, 7, 384-387) (Year: 2007).*

* cited by examiner

*Primary Examiner* — Sally A Merkling
(74) *Attorney, Agent, or Firm* — Craig Sherburne

(57) ABSTRACT

The present invention provides for a novel system and method for amplification and detection of nucleic acids within a miniaturized device wherein sample administration occurs via capillary forces through a channel created by drying a hydrogel containing all components needed for a cell-free, enzymatic, nucleic-acid amplification system other than the template nucleic acid or precursor thereto, and wherein an aqueous sample is provided to the desiccated hydrogel, and the hydrogel is rehydrated, through capillary forces.

27 Claims, 20 Drawing Sheets

(51) Int. Cl.
B01L 3/00 (2006.01)
B01L 9/06 (2006.01)
C12M 1/40 (2006.01)
C12M 3/06 (2006.01)
C12M 1/00 (2006.01)
*C12P 19/34* (2006.01)

(52) U.S. Cl.
CPC ... *B01L 2300/0838* (2013.01); *B01L 2300/12* (2013.01); *C12P 19/34* (2013.01)

2(a)

2(b)

2(c)

2(d)

3(a)  3(b)

3(c)

4(a)            4(b)

5(a)

5(b)

5(c)

5(d)

(a)

(b)

(c)

(a)

(b)

(c)

(d)

(a)

(b)

SEQUENCE LISTING

<160> NUMBER OF SEQ ID NOS: 15

<210> SEQ ID NO 1
<211> LENGTH: 20
<212> TYPE: DNA
<213> ORGANISM: Herpes Simplex Virus-1

<400> SEQUENCE: 1
gggccatttt acgaggagga 20

<210> SEQ ID NO 2
<211> LENGTH: 20
<212> TYPE: DNA
<213> ORGANISM: Herpes Simplex Virus-1

<400> SEQUENCE: 2
ggaacgcacc acacaaaaga 20

<210> SEQ ID NO 3
<211> LENGTH: 20
<212> TYPE: DNA
<213> ORGANISM: Herpes Simplex Virus-2

<400> SEQUENCE: 3
gtttggcgtg tgtctctgaa 20

<210> SEQ ID NO 4
<211> LENGTH: 20
<212> TYPE: DNA
<213> ORGANISM: Herpes Simplex Virus-2

```
<400> SEQUENCE: 4
cttttatccc cggcacacag                                              20

<210> SEQ ID NO 5
<211> LENGTH: 22
<212> TYPE: DNA
<213> ORGANISM: Ureaplasma urealyticum

<400> SEQUENCE: 5
ggaatgacac acgataaacc ct                                           22

<210> SEQ ID NO 6
<211> LENGTH: 22
<212> TYPE: DNA
<213> ORGANISM: Ureaplasma urealyticum

<400> SEQUENCE: 6
tgacaatcgc gcttctgtat aa                                           22

<210> SEQ ID NO 7
<211> LENGTH: 22
<212> TYPE: DNA
<213> ORGANISM: Mycoplasma hominis

<400> SEQUENCE: 7
aacgtaggtt gtactccgta ga                                           22

<210> SEQ ID NO 8
<211> LENGTH: 20
<212> TYPE: DNA
<213> ORGANISM: Mycoplasma hominis

<400> SEQUENCE: 8
aagtcggttt gctaacctcg                                              20

<210> SEQ ID NO 9
<211> LENGTH: 20
<212> TYPE: DNA
<213> ORGANISM: Homo sapiens

<400> SEQUENCE: 9
catggccatc cttgaagact                                              20

<210> SEQ ID NO 10
<211> LENGTH: 20
<212> TYPE: DNA
<213> ORGANISM: Homo sapiens

<400> SEQUENCE: 10
catggccatc cttgaagacc                                              20

<210> SEQ ID NO 11
<211> LENGTH: 20
<212> TYPE: DNA
<213> ORGANISM: Homo sapiens

<400> SEQUENCE: 11
atggcgcaga attacttaca                                              20

<210> SEQ ID NO 12
<211> LENGTH: 25
<212> TYPE: DNA
<213> ORGANISM: Homo sapiens
```

```
<400> SEQUENCE: 12
atcgccactt aatgaacctg tttcc                                              25

<210> SEQ ID NO 13
<211> LENGTH: 21
<212> TYPE: DNA
<213> ORGANISM: Homo sapiens

<400> SEQUENCE: 13
ctccttccta aactgtcctg a                                                  21

<210> SEQ ID NO 14
<211> LENGTH: 23
<212> TYPE: DNA
<213> ORGANISM: Homo sapiens

<400> SEQUENCE: 14
cgccacttaa tgaacctgtt tct                                                23

<210> SEQ ID NO 15
<211> LENGTH: 20
<212> TYPE: DNA
<213> ORGANISM: Homo sapiens

<400> SEQUENCE: 15
tccttcctaa actgtcctga                                                    20
```

SOLID GEL AMPLIFICATION METHOD AND APPARATUS FOR PLATFORM MOLECULAR DIAGNOSTICS

CROSS-REFERENCE TO RELATED APPLICATIONS

The present application claims priority from U.S. provisional patent application No. 61/697,194 filed Sep. 5, 2012 and U.S. provisional patent application No. 61/644,593 filed May 9, 2012, such applications are expressly incorporated by reference herein for all purposes.

FIELD OF THE INVENTION

The present invention pertains to the field of macro- and microfluidic devices and methods for detection of nucleic acids

BACKGROUND OF THE INVENTION

All of the publications, patents and patent applications cited within this application are herein incorporated by reference in their entirety to the same extent as if the disclosure of each individual publication, patent application or patent was specifically and individually indicated to be incorporated by reference in its entirety.

There is an increasing demand for a small scale array-based and/or microfluidic device that processes micro- or nano-volumes of sample, with time and cost savings arising from miniaturization. Prior art approaches to miniaturised polymerized chain reactions ("PCR") make use of open or enclosed chambers or flow through zones/channel networks with appropriate temperature regulation; some have on-board silicone rubber-based or magnetic-based valving and/or pumping. Although potentially powerful approaches, they have challenges such as pressure sealing, prevention of evaporation, pressure buffering, chemical interference through surface interactions, or contamination via the porous and gas permeable membranes used in pumps and valves.

Performing PCR in a colloidal hydrogel matrix (hereafter termed "hydrogel") confers a multitude of advantages. For example, the DNA, polymerase enzyme and other PCR reagents have reduced access to the device materials' surfaces where they may be adsorbed, absorbed, poisoned or otherwise rendered inactive; and are kept within close proximity to each other without the need for valves or pumps. Further, any contaminant solutes from device materials have reduced access to the PCR reaction.

As first introduced by Chetverin et al., gels provide a productive medium for PCR: see for example U.S. Pat. No. 5,616,478; which is herein incorporated by reference in its entirety. As described therein, PCR was confined to circular spots in a hydrogel sheet where the initial DNA or RNA templates, formed "molecular polonies" (short for polymerase colonies and named for their similarity to the growth of bacterial colonies in agar). As the initial amount of DNA can be accurately estimated by counting the number of polonies, Mitra et al. (Mitra, R. D. et al; *Nucleic Acid Research* 1999, 27, e34) performed DNA amplification in a thin acrylamide film polymerized with all the reagents along with plasmid. DNA as their template. In an alternate approach, Strizhkov et al. (Strizhkov, B. N. Et al; *Biotechniques* 2000, 29, 844-857) used nanoliter hydrogel pads to immobilize primers for PCR. Single Nucleotide Polymorphisms (SNPs) in cDNA were detected with polony technology by Butz et al. (Strizhkov, B. N. et al; 2000, 29, 844-857)

Recent advances have demonstrated that PCR can be performed in small volumes normally associated with microfluidic (sub-100 µl) reactions without the use of immobilized primers, as well as demonstrating that nucleic acids of sub-50 base pairs to megabase size can be administered to the surface of the hydrogel matrix with the nucleic acids capable of acting as a template to the remaining PCR reaction components internal to the hydrogel. See for example WO2012003579 by Atrazhev et al, or WO2012027832 by Atrazhev; which are herein incorporated by reference in their entirety.

The present art is in need of a means to perform analysis of amplicons generated by PCR, such as melting curve analysis ("MCA") without imposing additional steps for the transfer or handling of PCR product and to do so with a simplified process for administration of fluids for interrogation through PCR constrained within the hydrogel.

SUMMARY OF THE INVENTION

The present art has suffered from a lack of systems capable of automated manufacture, with simplified sample administration, capable of delivering fluid samples to a multiplicity of PCR ready hydrogel strips or hydrogel capillaries, wherein the samples may be unprocessed prior to administration.

In one aspect the present invention provides for a cassette for performing interrogations for the presence of a nucleic acid within an aqueous sample comprising an enclosing solid substrate; wax with at least one deformation on its surface; and a multiplicity of capillaries with two opposing apertures; wherein said capillaries contain a desiccated hydrogel containing all components needed for a cell-free nucleic acid amplification other than the template nucleic acid, within the capillaries there exists a space described by the inner diameter of said capillary and said desiccated hydrogel which allows atmospheric communication between opposing apertures and through said capillaries, said deformations are capable of receiving said capillaries, said deformations form a tight junction with the longitudinal surface of said capillaries and at least one end of said capillary is capable of receiving an aqueous sample, said wax with at least one deformation on its surface is contained within said solid substrate, said wax is optically transparent to at least two wavelengths of electromagnetic radiation wherein said at least two wavelengths are capable of differentiation by a recording device, and said enclosing substrate is capable of containing the wax when in a molten state. In one embodiment the wax is Paraffin wax. In a further embodiment said capillaries are less than 2 mm in diameter. In a still further embodiment said capillaries have an inner diameter of 1.1 mm. In another embodiment said enclosing solid substrate is thermally conductive. In a further embodiment said enclosing solid substrate is aluminum. In another embodiment said enclosing solid substrate absorbs electromagnetic radiation of at least one of said at least two wavelengths. In another embodiment said desiccated hydrogel is polymerized acrylamide and bis-acrylamide. In another embodiment said desiccated hydrogel is 4% acrylamide and 0.4% bis-acrylamide. In a another embodiment said components needed for a cell free nucleic acid amplification system comprises the enzymes, substrates and primers needed for a polymerase chain reaction. In a further embodiment said components needed for a cell free nucleic acid amplifications system comprises tris-sulfate, (NH4)2SO4, MgCl2, all four deoxyribonucleotides, Bovine Serum Albumin, at least two primers designed to hybridize with a target nucleotide sequence, a heat stable DNA polymerase, azobis, TEMED and water. In a still further embodiment said components needed for a cell free nucleic acid amplifications system includes LC Green.

In another aspect, the present invention provides for a device for performing an interrogation for the presence of a nucleic acid within an aqueous environment comprising a capillary with two opposing apertures that describes a sub milliliter volume that contains a desiccated hydrogel containing all components needed for a cell-free nucleic acid amplification other than the template nucleic acid wherein within the capillary there exists a space described by the inner diameter of said capillary and said desiccated hydrogel which allows atmospheric communication between opposing apertures and through said capillary. In one embodiment said capillary is less than 2 mm in diameter. In a further embodiment said capillary has an inner diameter of 1.1 mm. In another embodiment said desiccated hydrogel is polymerized acrylamide and bis-acrylamide. In a further embodiment said desiccated hydrogel is 4% acrylamide and 0.4% bis-acrylamide. In another embodiment said components needed for a cell free nucleic acid amplification system comprises the enzymes, substrates and primers needed for a polymerase chain reaction. In a further embodiment said components needed for a cell free nucleic acid amplifications system comprises tris-sulfate, (NH4)2SO4, MgCl2, all four deoxyribonucleotides, Bovine Serum Albumin, at least two primers designed to hybridize with a target nucleotide sequence, a heat stable DNA polymerase, azobis, TEMED and water. In a still further embodiment said components needed for a cell free nucleic acid amplifications system includes LC Green.

In another aspect, the present invention provides for a system for detecting the presence of a nucleic acid within an aqueous sample comprising wax with at least one deformation on its surface; an enclosing solid substrate; a multiplicity of capillaries with two opposing apertures; means for controlling temperature in thermal communication with said enclosing solid substrate; illumination means; and an optical detection means; wherein the amplification of a nucleic acid is detected through an increase in an optical signal received by said optical detection means resulting from the interaction of an illumination wavelength provided by said illumination means, said capillaries contain a desiccated hydrogel containing all components needed for a cell-free nucleic acid amplification other than the template nucleic acid, within the capillaries there exists a space described by the inner diameter of said capillary and said desiccated hydrogel which allows atmospheric communication between opposing apertures and through said capillaries, said deformations are capable of receiving said capillaries, said deformations form a tight junction with the longitudinal surface of said capillaries and at least one end of said capillary is capable of receiving an aqueous sample, said wax with at least one deformation on its surface is contained within said solid substrate, said wax is optically transparent to at least two wavelengths of electromagnetic radiation wherein said at least two wavelengths are capable of differentiation by a recording device, and said enclosing substrate is capable of containing the wax when in a molten state. In one embodiment the wax is Paraffin wax. In another embodiment said capillaries are less than 2 mm in diameter. In a further embodiment said capillaries have an inner diameter of 1.1 mm. In another embodiment said enclosing solid substrate is thermally conductive. In a further embodiment said enclosing solid substrate is aluminum. In another embodiment said enclosing solid substrate absorbs electromagnetic radiation of at least one of said at least two wavelengths. In another embodiment said desiccated hydrogel is polymerized acrylamide and bis-acrylamide. In a further embodiment said desiccated hydrogel is 4% acrylamide and 0.4% bis-acrylamide. In another embodiment said components needed for a cell free nucleic acid amplification system comprises the enzymes, substrates and primers needed for a polymerase chain reaction. In a further embodiment said components needed for a cell free nucleic acid amplifications system comprises tris-sulfate, (NH4)2SO4, MgCl2, all four deoxyribonucleotides, Bovine Serum Albumin, at least two primers designed to hybridize with a target nucleotide sequence, a heat stable DNA polymerase, azobis, TEMED and water. In a still further embodiment said components needed for a cell free nucleic acid amplifications system includes LC Green. In another embodiment said illumination means is a laser emitting light at a wavelength of 445 nm. In another embodiment said optical detection means is a CCD camera with a band-pass interference filter centered at 530 nm.

In another aspect, the present invention provides for a cassette for performing interrogations for the presence of a nucleic acid within an aqueous sample comprising an enclosing solid substrate; wax with at least one deformation on its surface; a multiplicity of hydrogel strips; wherein said hydrogel strips comprise a desiccated hydrogel containing all components needed for a cell-free nucleic acid amplification other than the template nucleic acid, said hydrogel strips are present within a volume described by said deformation present on the surface of said wax and a viewing window which forms a tight junction with the surface of the wax, at least two apertures are present in said volume, said apertures are in atmospheric communication with at least one other aperture, said wax with at least one deformation on its surface is contained within said solid substrate, said wax is optically transparent to at least two wavelengths of electromagnetic radiation wherein said at least two wavelengths are capable of differentiation by a recording device, said viewing window is optically transparent to at least two wavelengths of electromagnetic radiation wherein said at least two wavelengths are capable of differentiation by a recording device, and said enclosing substrate is capable of containing the wax when in a molten state. In one embodiment said hydrogel is bound to said viewing window. In another embodiment the wax is Paraffin wax. In another embodiment said enclosing solid substrate is thermally conductive. In a further embodiment said enclosing solid substrate is aluminum. In another embodiment said enclosing solid substrate absorbs electromagnetic radiation of at least one of said at least two wavelengths. In another embodiment said desiccated hydrogel is polymerized acrylamide and bis-acrylamide. In a further embodiment said desiccated hydrogel is 4% acrylamide and 0.4% bis-acrylamide. In another embodiment said components needed for a cell free nucleic acid amplification system comprises the enzymes, substrates and primers needed for a polymerase chain reaction. In a further embodiment said components needed for a cell free nucleic acid amplifications system comprises tris-sulfate, (NH4)2SO4, MgCl2, all four deoxyribonucleotides, Bovine Serum Albumin, at least two primers designed to hybridize with a target nucleotide sequence, a heat stable DNA polymerase, azobis, TEMED and water. In a still further embodiment said components needed for a cell free nucleic acid amplifications system includes LC Green.

In another aspect the present invention provides for a system for detecting the presence of a nucleic acid within an aqueous sample comprising wax with at least one deformation on its surface; an enclosing solid substrate; a multiplicity of hydrogel strips; means for controlling temperature in thermal communication with said enclosing solid substrate; illumination means; and optical detection means; wherein the amplification of a nucleic acid is detected through an increase in an optical signal received by said optical detection means resulting from the interaction of an illumination wavelength provided by said illumination means, said hydrogel strips comprise a desiccated hydrogel containing all components needed for a cell-free nucleic acid amplification other than the template nucleic acid, at least two apertures are present in said volume, said apertures are in atmospheric communication with at least one other aperture, said wax with at least one deformation on its surface is contained within said solid substrate, said wax is optically transparent to at least two wavelengths of electromagnetic radiation wherein said at least two wavelengths are capable of differentiation by a recording device, and said enclosing substrate is capable of containing the wax when in a molten state. In one embodiment the wax is Paraffin wax. In another embodiment said enclosing solid substrate is thermally conductive. In a further embodiment said enclosing solid substrate is aluminum. In another embodiment said enclosing solid substrate absorbs electromagnetic radiation of at least one of said at least two wavelengths. In another embodiment said desiccated hydrogel is polymerized acrylamide and bis-acrylamide. In a further embodiment said desiccated hydrogel is 4% acrylamide and 0.4% bis-acrylamide. In another embodiment said components needed for a cell free nucleic acid amplification system comprises the enzymes, substrates and primers needed for a polymerase chain reaction. In a further embodiment said components needed for a cell free nucleic acid amplifications system comprises tris-sulfate, (NH4)2SO4, MgCl2, all four deoxyribonucleotides, Bovine Serum Albumin, at least two primers designed to hybridize with a target nucleotide sequence, a heat stable DNA polymerase, azobis, TEMED and water. In a still further embodiment said components needed for a cell free nucleic acid amplifications system includes LC Green. In another embodiment said illumination means is a laser emitting light at a wavelength of 445 nm. In a further embodiment said optical detection means is a CCD camera with a band-pass interference filter centered at 530 nm.

In another aspect, the present invention provides for a cassette for performing interrogations for the presence of a nucleic acid within an aqueous sample comprising an solid substrate with at least one deformation on its surface; a multiplicity of capillaries with two opposing apertures; wherein said capillaries contain a desiccated hydrogel containing all components needed for a cell-free nucleic acid amplification other than the template nucleic acid, within the capillaries there exists a space described by the inner diameter of said capillary and said desiccated hydrogel which allows atmospheric communication between opposing apertures and through said capillaries; said deformations are capable of receiving said capillaries, and said deformations form a tight junction with the longitudinal surface of said capillaries and at least one end of said capillary is capable of receiving an aqueous sample.

DETAILED DESCRIPTION OF THE PRESENT INVENTION

Figure 1:
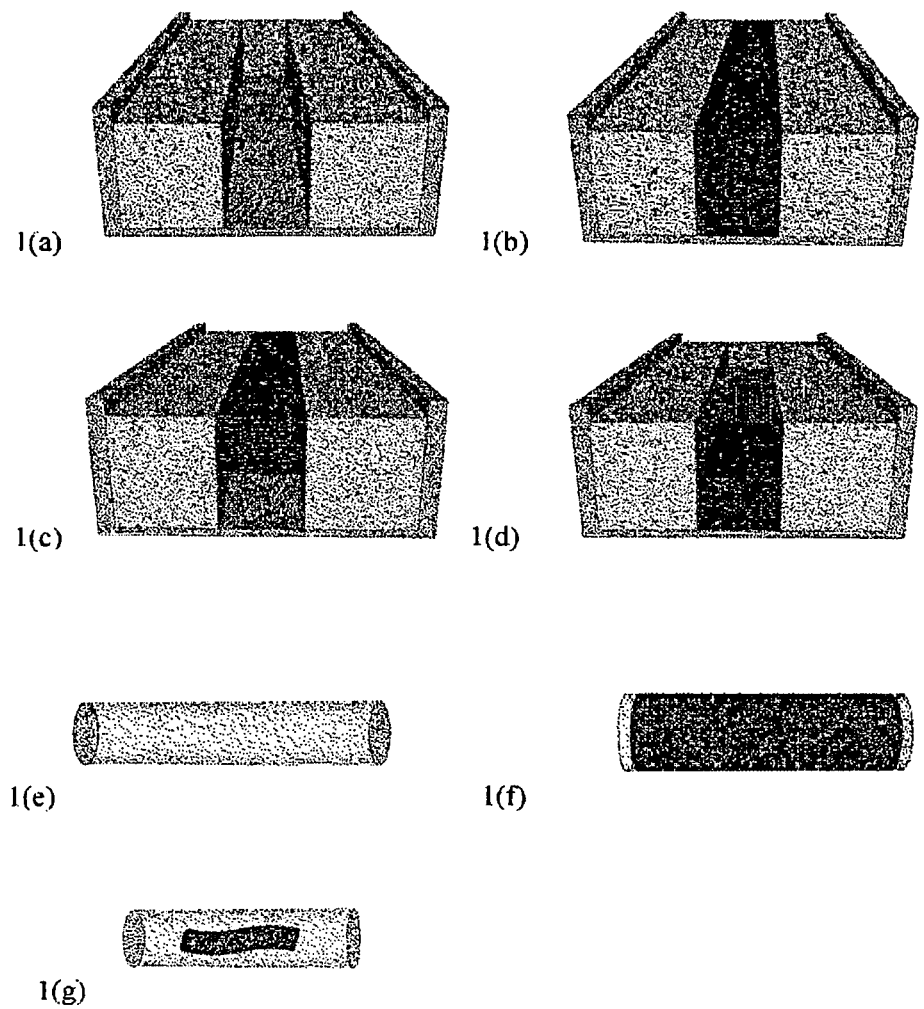
FIG. 1 shows a trench made from wax/glass, plastic/glass for the PCR reaction mix to be polymerized in (a-d) a hydrogel strip and (e-g) a capillary.

The prior art has described hydrogel-based PCR systems incorporating multiparameter PCR on individual reaction units termed hydrogel posts, using mineral oil as the vapour barrier. While this proved to be a reliable strategy, the "gel post chips" described in the art are not readily manufacturable and the use of oil creates problems for handling of a packaged cassette. To provide a system that could be easily manufactured, the present invention provides for a cassette comprised of hydrogel in capillaries or contained in a trench defined by a supporting substrate; with each capillary or trench segment defining a "hydrogel strip" serving as an individual reaction unit with a specified primer set, and further desiccated as described herein or otherwise known in the art. A chosen complement of capillary reaction units with the required primer sets can be assembled in wax trenches; or the wax may be used as the supporting substrate to define a hydrogel strip as further described herein. The wax then confines capillaries in the trench, thereby enclosing them in a cassette, said cassette comprising the hydrogel strip or hydrogel within a capillary as appropriate, the wax and an enclosure with at least one side capable of providing optical communication. Capillaries or gel strips can also be assembled in trenches without the use of wax, by way of non-limiting example, through use of a viscous material to maintain the capillary or gel strip in position them in place as described herein, or in another embodiment by placing them snugly in the trench. When PCR cycling begins, the wax melts and creates a vapour barrier; said wax chosen in accordance with that described herein, specifically to be solid at expected transport temperatures, liquid at expected PCR temperatures and optically transparent to wavelengths used to monitor or detect the effects of the PCR. Advantageously when PCR is complete, the wax solidifies and allows safe disposal of used cassettes. Other ways of preventing evaporation during thermal cycling are also contemplated by the present invention, as would be known in the art. The cassette can be stored at ambient temperature and later rehydrated by raw sample. Desiccation enables rapid sample delivery, with the shrinkage of the hydrogel from the desiccation. As described herein, the drying was performed to create a channel within each capillary that allows raw sample to enter via capillary action. A given cassette can test multiple patient samples, multiple sample types, test for the presence of multiple targets, or combinations thereof; with no significant cross-contamination. Each cassette may include quality control verification through integrated positive and negative controls for each target. The desiccated reaction units are stable over time at ambient room temperature as well as at 4° C. and at −20° C., thus enabling "on the shelf" storage of assembled cassettes.

Specifically, the novel method and apparatus described herein provides for the performance of PCR or other amplification or gene detection method in a hydrogel medium, that in one embodiment is less than 50 μL in volume, in a preferred embodiment is between 10-25 μL in volume and in an even more preferred embodiment is 13 μL in volume, obtaining real-time data in situ by detecting the fluorescence of DNA in the presence of an intercalating dye or other means of product or amplicon detection, and further simplifying the process for administration of a sample for interrogation under PCR followed by, or concurrent with, detection methods such as MCA. By utilizing the techniques described herein, a single administration of sample for interrogation, or a number of simplified administrations, can be used for multiple interrogations; allowing a single administration step for performing concurrent sample interrogation with positive and negative controls, multiple redundant interrogations, or multiple disparate interrogations; all detecting the presence of certain nucleic acid templates within a sample.

As used herein, "hydrogel" refers to hydrophilic polymers forming colloidal hydrogel matrixes which result in similar mobilities of the nucleic acids of sizes contemplated by the present invention as in the specifically described gels herein, by way of non-limiting example, polyacrylamide and polyvinylpyrrolidone ("xPVP") cross-linked with PEG-diacrylate resulting from the photopolymerization of 3.3% vinylpyrroledone with 0.7% Polyethyleneglycol-diacrylate.

The system described herein is designed to facilitate performance of diagnostic tests in parallel on the same sample, or on multiple different samples, using different hydrogel filled reaction chambers, with a simplified sample administration process. A non-limiting example of the utility of this platform is testing of patients as they present in the clinic, or in "near point of care" settings as they are known in the art, rather than transport of patient samples to a distant or centralized laboratory. The ability to acquire real-time template amplification, in one embodiment by PCR, and MCA using the method and apparatus of the present invention expands the use of this technique to applications such as asymmetric PCR for mutation scanning and genotyping performed with unlabelled probes. The utility of the present invention is not confined to detection of nucleic acids within a healthcare or human health setting. It is contemplated that the present invention has utility with respect to environmental, veterinary and any other field where interrogation for the presence of nucleic acids within a sample containing water.

The novel hydrogel PCR system of the present invention can perform PCR, melt curve analysis and real time quantitative PCR, with an output that compares favourably with conventional systems. It is contemplated by the present invention that both processed, and unprocessed, aqueous or partially aqueous samples may be used with the present method and apparatus, including but not limited to, serum, plasma, whole blood, sputum, mucous, aspirates, debrided tissue, scrapings, lymphatic fluid, macerated plant tissue, suspensions of fecal matter, soil samples and environmental water samples. The present invention contemplates use of methods for detecting a gene or transcript other than PCR and one skilled in the art would be aware of the variations of PCR and other gene or transcript detection systems. By performing replicate PCRs in multiple hydrogel reaction chambers, statistical data to confirm a result can be obtained. The method of the present invention can be implemented for detection in the same sample of multiple nucleic acids, mutations/polymorphisms or other genetic changes in DNA, RNA or during RNA processing as known in the art, contained within a heterogeneous nucleic acid population, or multiple organisms, pathogens, bacteria or viruses within a single sample, or can accommodate testing of multiple samples, each for more than one target template.

The present invention provides a method of performing real-time PCR in hydrogels with MCA in an array of cylindrical or other shaped hydrogel-filled or self-standing hydrogel reaction chambers (for example sub-milliliter volumes per reaction chamber, such as hydrogel posts, hydrogel filled cylinders, hydrogel strips). In a preferred embodiment the PCR and post-PCR analysis of the resulting amplified nucleic acid (if any) was performed in a range of microfluidic volumes (sub-one milliliter volumes).

The present invention provides a method of performing real-time PCR and MCA in a hydrogel containing all PCR reagents, save for the template, which can be made in a variety of shapes or sizes and such hydrogels desiccated, thereby reducing its volume. When a hydrogel is polymerized and desiccated inside a constrained channel space, the reduction of the hydrogel volume results in an empty space that can be used for the sample delivery through capillary forces, which serves to rehydrate the hydrogel. The capillary forces therefore simplify the application of sample for interrogation through PCR within the hydrogel.

The desiccation contemplated by the present invention is not limited to any one known generally in the art. One skilled in the art will recognize that although there is a multiplicity of desiccation methods and strategies that may be used, the exact method selected should be one that maintains the integrity of the hydrogel, is non-destructive to the PCR reagents within, and will allow successful PCR following rehydration and introduction of a template. One example of a methodology is presented in U.S. Pat. No. 6,313,102.

The contained channel can be formed from any number of solid substrates, and in a preferred embodiment the substrate is wax or glass, plastic, such as Poly(methyl methacrylate (PMMA), Cyclo Olefin Polymer (COP), cyclic olefin copolymer (COC), Polycarbonate (PC), Polystyrene (PS), or other thermally conductive composite polymers, metal-plastic alloys, or ceramic, forming a trench within the substrate and may optionally be covered. The solid substrate may also be formed of metal shaped to include trenches, for example aluminum or injection moldable metals. In a preferred embodiment the covering is transparent to the wavelengths of light used to perform MCA, or other means of detection of the presence or absence of a PCR product of interest. In another embodiment, an underlying substrate is established in wax, plastic such as PMMA, COP, COC, or composite polymers, glass, metal such as aluminum, upon which is placed a capillary tube formed by glass or plastic containing a desiccated hydrogel, or a strip of hydrogel containing reagents, as contemplated by the present invention. It is contemplated by the present invention that the hydrogel may be attached to the substrate or the optional covering such as a glass coverslip or clear plastic, or may form a direct adhesion to the substrate and cover, respectively below and above the hydrogel reaction chamber and as further described herein. Wax may be used to anchor reaction chambers within the substrate. A wax covering also provides a vapour barrier when it melts, as heating cycle initiates for PCR. The hydrogel containing capillary is contemplated as being in various shapes (including, but not limited to, round, oblong, square, or rectangular) and can be made with different glass types and may optionally be surrounded by a plastic cladding. Hydrogel strips without a glass or other cladding can also be formed directly in the trenches. The wax or plastic trenches used to constrain clad hydrogels and/or directly form the hydrogels (herein referred to as "hydrogel strips") can be in various shapes (including but not restricted to rectangular, square, semi-oblong, or semi-circular). Each capillary or hydrogel strip can be of various lengths and heights, though the dimensions are constrained by the ability to draw sufficient fluid into the hydrogel strip or capillary through capillary forces, and as such are a function of the viscosity of the fluid, air pressure, ambient humidity, and other factors known in the art to affect capillary forces. Therefore in a preferred embodiment of the present invention the trench or capillary containing a hydrogel describes a microfluidic volume so as to reduce environmental effects on capillary forces as well as ensure sufficient capillary forces to allow introduction of the fluid to the desiccated hydrogel, with an opening that allows administration of the sample and another opening to allow displaced air to escape, thereby enabling capillary flow through the channel.

With respect to the gaps established between adjacent capillaries, one skilled in the art will recognize that the extent of gap necessary to isolate adjacent capillaries, with respect to fluid communication of a hydrating sample between adjacent capillaries; or alternatively to allow fluid communication of a hydrating sample between adjacent capillaries; is a function of the ambient air pressure, viscosity of the hydrating sample, and humidity of the atmosphere surrounding the capillaries. Though a failure of hydrating sample to successfully communicate through adjacent capillaries is easily addressed by administering sample to the non-hydrating channel, reproducibility and ease of sample administration to a multiplicity of adjacent capillaries (enabling fluid communication therein) is enhanced by maintaining a separation of less than 1.5 mm, and in a preferred embodiment, no more than 1 mm with respect to a 1.1 mm diameter capillary tube. Air gaps of greater than 1.5 mm, and in a preferred embodiment greater than 3 mm, are recommended in order to isolate adjacent capillaries and prevent fluid communication. Capillaries of greater than 1.1 mm are contemplated by the present invention; though larger hydrogels require extended periods for desiccation; the only constraint is creation of a sufficient space for delivery of sample via capillary forces of a sufficient volume to rehydrate the desiccated hydrogel.

The present invention contemplates an assembly of, for example, hydrogel strips or hydrogel containing capillaries to produce a diagnostic "cassette" (or "chip") with the hydrogel strips or hydrogel containing capillaries embedded in a wax, plastic, metal, glass, ceramic, metal/wax, plastic/wax, glass/wax or plastic/metal/wax substrate and desiccated, wherein the diagnostic cassette can be stored and be ready for accepting samples and in combination with an internal or external heating and visualization system, and be capable of performing an interrogation upon a clinical sample or samples in a clinical, or other, settings. The layout of the hydrogel strips or capillaries in wax, other solid material, or wax in combination with other solid supporting substrates can be in various forms including but not limited to those resembling the petals of a flower, alignment in a row, and parallel arrangements; so long as there is a space for introduction of the sample for interrogation and a path for movement of displaced air resulting from the drawing and rehydration of the hydrogel by capillary forces. Such a path can be provided by openings at both ends of a capillary or gel strip reaction unit. It is contemplated by the present invention that rehydration of the desiccated hydrogel can be controlled through the size and air pressure of said path for displaced air resulting from the rehydration of the hydrogel. Advantageously, the chip containing, for example, the hydrogel strips or hydrogel capillaries in a wax, plastic, metal, glass, ceramic, wax/plastic, wax/plastic, or wax/plastic/metal media are capable of being manufactured using automated processes and the materials used in the manufacture are relatively inexpensive. The channels or trenches contemplated herein may be formed using hot embossing, stamps that can be made of materials such as polydimethylsiloxane (PDMS), or other methods to form metal or plastic or other materials as solid supporting substrates.

Wax housing embedded or attached hydrogel strips or hydrogel capillaries can be placed in a solid supporting substrate such as an aluminum or plastic pan. A seal, for example PDMS, is used as a stamp to indent the melted wax in the pan to form impressions for placing hydrogel capillaries or forming hydrogel strips in various arrangements. Hydrogel capillaries or hydrogel strips are placed at the bottom of the solid supporting substrate such that no wax is directly touching the liquid sample above the hydrogel. This prevents the reaction chambers (e.g. hydrogel capillaries or hydrogel strips) from "floating" on a thin layer of wax when the wax melts. Reaction units can also be anchored to the bottom surface of the support using, for example, 40% trehalose or other sugar or a drop of monomeric PDMS, for example Sylgard 184 silicon elastomer base, Dow Corning Corporation, Midland, USA. In another embodiment, wax on both sides of the trench walls are compressed around the capillaries to anchor them after they have been placed in the trench. The fixed position of a reaction chamber enhances thermal communication with the heating element and enables precise PCR cycling and accurate imaging of fluorescence during PCR and MCA. The indentation of the wax for placing different shapes of capillaries must precisely match the width of the capillary, such that there is no extra gap between/through which the sample could otherwise flow; this prevents the fluid sample from spreading outside the immediate confines of the reaction chambers where any unabsorbed sample could facilitate components of one hydrogel moving into another. A close fit between the trench and the hydrogel reaction chambers facilitates the absorption of the entire introduced sample volume by the desiccated hydrogel with no excess fluid remaining, thereby preventing any possibility of cross contamination between reaction chambers. Among possible configurations of reaction chambers, each chamber may incorporate different primers, allowing multiple reaction chambers in close proximity to each other within a given chip or cassette assembly. Thus fluid contact between them is disadvantageous, and the presence of molten wax upon heating for the PCR, as contemplated by the repent invention, advantageously inhibiting fluid communication between reaction chambers. When multiple samples are tested on a single substrate chip or cassette holding multiple different reaction vessels, it is important to ensure that no sample mixing occurs, again emphasizing the disadvantage of having unabsorbed free fluid on/in the substrate of the chip or cassette.

The hydrogel strips are made in the solid supporting substrate containing trenches which act as a mold for polymerized hydrogels, while hydrogel capillaries can be polymerized and desiccated within the trenches present in the solid supporting substrate or prepared elsewhere and later placed within the trenches. Reagent-containing hydrogels can be polymerized in wax, plastic, metal or other material used to form a "mold". For hydrogel capillaries prepared elsewhere and later placed into the trenches, the hydrogel capillaries can be attached to the bottom of the trench by polymerized or dried acrylamide solution, monomeric PDMS, or dried sugar solution such as trehalose. In another embodiment, wax can be added atop the hydrogel capillaries in the trench or the wax walls can be compressed to fix them into position and to provide a vapour barrier when melted.

It is contemplated by the present invention that each hydrogel capillary or hydrogel strip within a solid supporting substrate, or diagnostic chip, may have different primers for amplifying different segments of a nucleic acid which may, or may not be present within a sample for interrogation, thereby allowing detection of the presence of nucleic acids which are known to correlate to disease states, congenital or otherwise, as well as infections, or generally conditions that correlate with the presence of a given nucleic acid marker. A single diagnostic cassette can contain different hydrogel strips or hydrogel capillaries with different primers for analysing a single patient sample, multiple samples from a single patient, or multiple samples from multiple patients. Each hydrogel capillary or strip can have different primer sets for assembly in an array of reaction chambers (a chip or cassette) that together carry out simultaneous testing in parallel for multiple targets, each in a different reaction chamber but all on the same substrate. For a given chip or cassette that includes multiple trenches or their equivalent, an assembled substrate can include positive and negative controls that are simultaneously tested in parallel with the test capillaries. For example, a given set of trenches might each contain a series of test capillaries aligned next to each other or angled beside each other, as well as positive and negative controls, such that a different patient sample can be applied to each trench, or many different targets and their respective controls can be tested for a single patient sample. Sample delivery can be performed to a single hydrogel capillary at a time or to a multiplicity of hydrogel capillaries in fluid communication with a single source of fluid sample. Multiple hydrogel capillaries or hydrogel strips within a solid supporting substrate or diagnostic chip may have different primers to detect the presence of certain nucleic acids using PCR from one patient sample, or multiple alignments or arrangements to diagnose several or many patients. Positive and negative controls can be included in the same solid supporting substrate or diagnostic chip through selection of primers or PCR components present within the hydrogel strip or hydrogel capillary, as is generally known in the art.

Advantageously, during the PCR hydrogel strips or hydrogel capillaries are housed within wax selected for a melting point lower than the lowest temperature used within PCR cycling and selected for optical transparency of the relevant wavelengths used for MCA; the melted wax closes the open ends of the hydrogel strips or hydrogel capillaries or enters the ends of the hydrogel capillaries establishing them as individual reaction chambers. The wax thereby acts as a barrier to stop cross contamination of among different primer sets and/or different samples analysed on the same chip as well as preventing hydrogel drying during the PCR or MCA. If housing the hydrogel strips or hydrogel capillaries in a plastic or metal or metal/plastic substrate, it may have a wax cap placed over the hydrogel strips or hydrogel capillaries such that wax, once melted, can enclose them. Microfluidic channels can be incorporated into plastic or metal substrate to hydrate multiple strips with the sample by dispensing it from one opening.

When a desiccated hydrogel in a capillary is hydrated by a sample, the fluid fills around the dried gel, thereby hydrating the gel. For a sample that contains biological substances or particulates that are opaque or illumination-opaque or transmission-opaque with respect to fluorescence or illumination wavelength; by way of non-limiting example, red blood cells or other components in, for example, the blood or particulates in for example fecal suspensions or plant material; these cannot be absorbed into the hydrogel as those substances are retained in the perimeter of the inside of the capillary. These substances then act as light blockers preventing excitation light reaching the hydrogel or the fluorescent light exiting from the hydrogel resulting in low light intensities measured by the detector. Advantageously this phenomenon can be prevented through attachment of the hydrogel to the inside capillary surface during the polymerization and desiccation. With respect to the hydrogel strips of the present invention, the desiccated hydrogel is attached to the glass from the top side, allowing the sample to flow beneath as it hydrates the gel, thereby restricting optically opaque materials to the bottom of the chamber and allowing fluorescence measurements to be made on the top side. Advantageously, if the sample contains opaque substances, those substances are trapped at the bottom of the hydrogel strip or other configuration, leaving the top side of the hydrogel strip attached to the optically clear glass or other substrate. In such case, the excitation light can reach the hydrogel and the fluorescence light generated in the hydrogel can exit the hydrogel through the top side of the strip without any obstruction allowing the collection of accurate signals during the DNA amplification or the melting curve analysis.

The solid supporting substrate housing the hydrogel strips or hydrogel capillaries may have channels indented into the substrate forming the hydrogel strips within the channels or the hydrogel capillaries may be placed within the channels. Walls of these channels can reduce the light bleeding from one strongly fluorescing capillary to the others proximal to it during the laser induced fluorescence, or other optically based measurements, as long as at least one optically-transparent region is present to allow transmission of illumination or fluorescence emissions to a collector. Such a solid supporting substrate can contain a higher density of hydrogel strips or hydrogel capillaries thereby allowing more reactions within a diagnostic chip. Opaque barriers may be placed between the hydrogel capillaries or hydrogel strips lanes to reduce optical bleed. Coloured wax or plastic can also be used to reduce optical bleeding between hydrogel capillaries.

In one embodiment, the present invention provides for a ready-made cassette containing short glass capillaries holding desiccated acrylamide gels containing all reagents required for undertaking a PCR reaction, save for the DNA template. The cassettes are arranged in wax trenches created within metal pan, or structure capable of containing the wax and cassettes when said wax is in a molten state. Positive and negative controls are included as part of the cassette. In one non-limiting embodiment described herein, the capillaries within the cassette contain reagents for detecting four sexually transmitted infections using unprocessed aqueous specimens from a human. To increase the stability during storage of the cassettes, the hydrogel mixture inside capillaries is desiccated prior to cassette assembly and the final cassette is stored under vacuum, such as within a vacuum-packed plastic enclosure known in the art. When testing occurs, the cassette is removed from the enclosure and sample containing the templates is introduced to the desiccated hydrogel mixture by capillary action to rehydrate the capillaries.

The present invention contemplates using an increase in an optical signal as an indication of the amplification of a target nucleotide sequence as a result of an amplification reaction resulting from the binding of primers selected to amplify only a target sequence. One skilled in the art will recognize that there are a multitude of technologies available to provide said optical signal, and the present invention is not intended to be limited to those described herein. In a preferred embodiment, the present invention utilizes a construct that provides an optical signal when interacting with double stranded DNA, which is absent or attenuated when said DNA is single stranded. This provides the ability to monitor the transition of DNA from double- to single-stranded and allows MCA as contemplated herein. As such, LC Green, an intercalating dye which provides an optical signal due to increased fluorescence when intercalated with dsDNA, provides such a result, though the present invention contemplates the use of any dye or marker construct, such as quantum dots; such constructs or dyes selected according to the transparency of the wax described herein to the resulting optical signal. Care must also be paid to the transparency of the wax to the wavelength of light or other electromagnetic radiation utilized to provide said optical signal. As used herein "illumination means" may be any source of energy or electromagnetic wave that is utilized to provide an input energy which is then transformed, attenuated, or modified by the dye or construct to provide the optical signal. Examples of illumination means include, but are not limited to, lasers, light emitting diodes, bulbs and energetic chemical bonds.

Example 1: Sample Delivery

A channel with dimensions such that it contains microfluidic volumes (i.e. sub-1 mL volumes) or a "microfluidic channel", can be made in wax, plastic, glass, wax/glass or wax/plastic (FIG. 1(a)) into which can be placed a hydrogel to make hydrogel strips, or alternatively into which can be placed capillary tubes, as generally known in the art, filled with hydrogel plugs (FIG. 1(e). As shown in FIG. 1(a), a trench is made from wax/glass, plastic/glass, metal, metal/plastic, ceramic, or clear plastic for the PCR/hydrogel mix to be polymerized. FIG. 1(b) illustrates the reaction mix filled and polymerized to create the hydrogel; with FIG. 1(c) showing the desiccated hydrogel attached to the coverslip or clear plastic on the top, or the bottom of the plastic or pan or the glass capillary tube (FIG. 1(d)). FIG. 1(e) shows a glass capillary, which is then filled with hydrogel with PCR reaction mix and then polymerized into a hydrogel (FIG. 1(f)), and desiccated hydrogel in the capillary (FIG. 1(g)).

A PCR/hydrogel mix can be supplied to a wax channel or other type of trench as an enclosure (FIG. 1(b)) forming a "hydrogel strip" or into a capillary tube (FIG. 1(f)) forming a hydrogel capillary, drawn by capillary forces. Upon desiccation of such a hydrogel, the hydrogel strip (FIG. 1(c) and FIG. 1(d)) or hydrogel capillary (FIG. 1(g)), a path or channel is created that can be used to deliver a water-based sample, by capillary forces. As the sample is drawn into the path or channel by capillary forces the hydrogel hydrates to its full size without leaving any excess liquid sample. The sample can then be interrogated by PCR as contemplated in the art.

Example 2: Chip or Cassette Containing Hydrogel Strips or Capillaries

Figure 2:
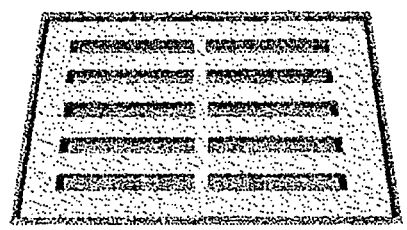
FIG. 2 shows the filling of a hydrogel strip where wax or plastic trenches are made in wax or plastic.
Figure 2:
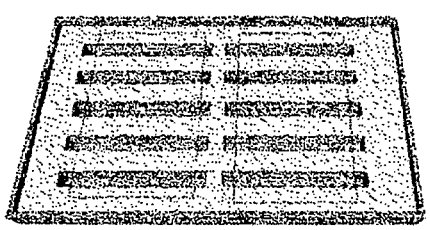
Figure 2:
Figure 2:
Figure 3:
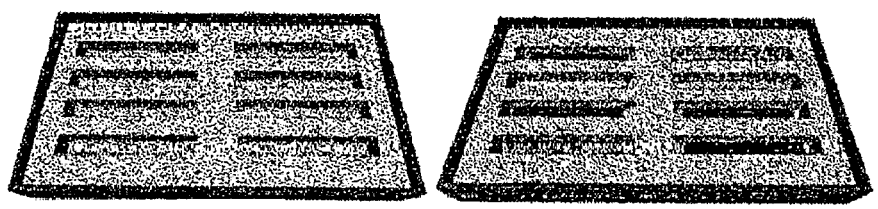
FIG. 3 shows trenches made in a pan by pressing the melted wax by a PDMS seal or by injection molding of the plastic.
Figure 3:
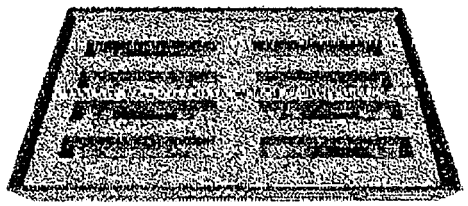

A diagnostic cassette can be made by indenting wax with a PDMS stamp to produce trenches for making hydrogel strips (FIG. 2(a)) or housing hydrogel capillaries (FIG. 3(a)). FIG. 2(a) shows the filling of a hydrogel strip where wax or plastic trenches are made in wax, metal, or plastic, while FIG. 2(b) shows how a coverslip/clear plastic strip is placed by heating wax or sticking to plastic or metal to make channels, channels are filled with PCR/hydrogel reaction mix by capillary forces and polymerized into gels (FIG. 2(c)), and desiccation of the hydrogel inside the channels creates a path that allows the sample to be delivered and the hydrogel to be hydrated (FIG. 2(d)). FIG. 3(a) shows trenches made in a pan by pressing the melted wax by a PDMS seal or by injection molding of the plastic, while FIG. 3(b) shows the capillaries filled with reaction mix that are polymerized in the trenches or alternatively polymerized prior to placement in trenches, and hydrogels are desiccated inside the capillaries or gel strips are dried in their trenches (FIG. 3(c))

The shape of the hydrogel strip may be controlled by altering the shape of the PDMS stamp, as the stamp produces the reverse shape within the trench. The shape of the PDMS stamp should match the shape of the capillaries such that the capillary lies snugly in the created wax or plastic trench. A plastic or metal diagnostic chip, with or without coloring to block any optical bleeding, can be made with techniques such as injection molding, heat embossing, milling or other known methods, so as to produce trenches for hydrogel strip formation or for placement of hydrogel capillaries. Different hydrogel capillaries or hydrogel strips can have different primers for testing different diseases or conditions. The glass coverslip or a clear plastic strip (FIG. 2(b)) on wax can be placed by heating the wax selectively or on plastic by gluing with UV epoxy or solvent bonding. As shown in FIG. 2(c), the channels are filled with an unpolymerized hydrogel containing PCR reaction mix, by capillary forces and polymerized into gels. FIG. 2(d) illustrates after desiccation of the gel, with the inside of the channel describing a path that allows the sample to be delivered and the hydrogel to be hydrated. In the present case, the size of the desiccated gel within a capillary in a preferred embodiment is about 0.7 mm, creating a channel sufficiently wide to allow effective movement of fluid through the channel and expelling of air.

Figure 7:
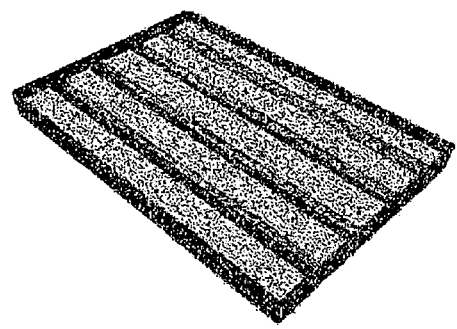
FIG. 7 shows the preparation of hydrogel strips.
Figure 7:
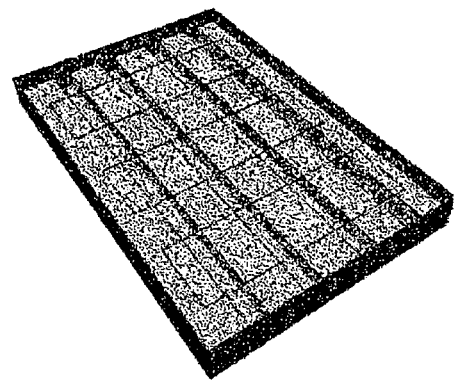
Figure 7:
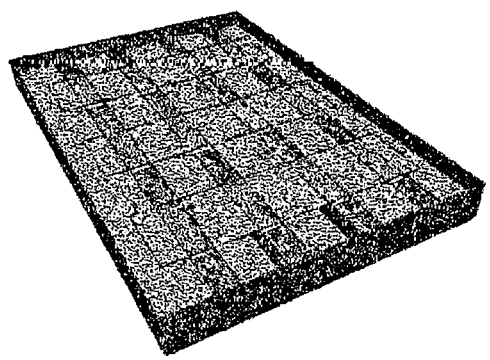

Specifically, the manufacture of hydrogel strips in accordance with the present invention is as follows. As shown in FIG. 7(a), wax imprints are made in a thermally conductive pan, similar to those described herein for the purposes of holding and/or stabilizing capillaries. As shown in FIG. 7(b) a plastic or glass strip is placed perpendicular to the direction of the channels imprinted within the wax. The plastic or glass strip is selected so as to be optically transparent to the selected excitation and fluorescence wavelength used for the detection and monitoring of the PCR nucleotide amplification and MCA. The glass or plastic strips may be treated to increase and enhance binding of the hydrogel to the strip during polymerization and desiccation, similarly the optically transparent covers described herein may be treated similarly. Such treatment may comprise a "bind silane" method, as generally known in the art and is generally described as follows. The surface of the strips are treated to enhance adherence to the hydrogel by immersing them in a mixture of 40 mL of 95% ethanol, 1 mL of 100% acetic acid (Fluka, Buchs, cat#45725), 8.9 mL of water, and 100 µL of 3-(trimethoxysilyl)propyl methacrylate (Sigma, cat#440159) for 1 hour; followed by washing with isopropanol (2-propanol).

Figure 8:
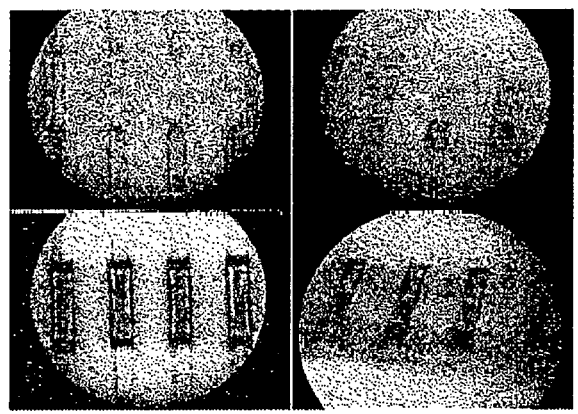
FIG. 8 shows (a) administration of complex and fluorescence opaque sample to a hydrogel strip of the present invention, (b) results of PCR, (c) increase of fluorescence and (d) MCA.
Figure 8:
Figure 8:
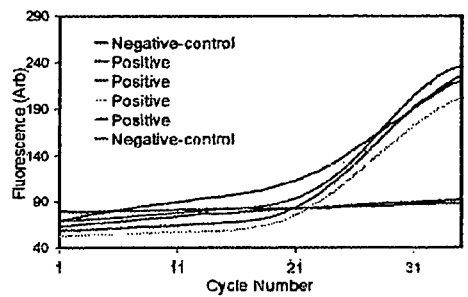
Figure 8:
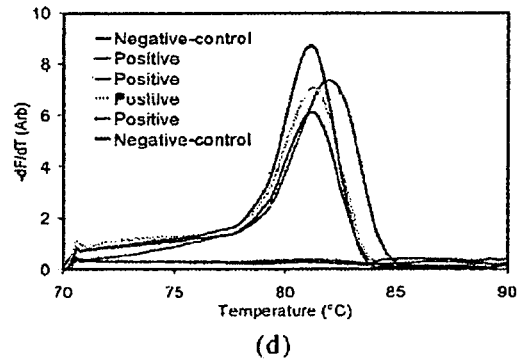

As shown in FIG. 7(c) the hydrogel reaction mixture, as further described in Example 6 herein, is added and polymerization initiated or allowed to occur; followed by desiccation as known in the art, se by way of non-limiting example Rossi, S., et al *Biotechnol. Prog.* 1997, 13, 609; Kaijalainen, S. Et al *Nucleic Acids Res.* 1993, 21, No. 12, 2959; Roser, B., *BioPharm*, September 1991, 47; Carpenter, J. F., et al *Cryobiology,* 24, 455; and U.S. Pat. No. 6,313,102. Delivery of a hydrating sample is performed under the glass or plastic strip with the adherent desiccated hydrogel, resulting in any obfuscating, confounding or opaque elements within the hydrating sample remaining under the rehydrated hydrogel. Therefore obfuscating, confounding or opaque materials within complex samples such as blood, stool, water containing significant particulate matter, macerated plant tissue, or aqueous suspensions of soil or other particulate matter; are advantageously constrained within the side opposing the transparent glass or plastic slide and therefore on the side opposing the illumination source and fluorescence detection contemplated by the present invention. FIG. 8(a) shows desiccated hydrogel strips (top) and the hydrogel strips following administration of blood as a hydrating sample (bottom). FIG. 8(b) shows a fluorescence image taken at the 35$^{th}$ cycle of PCR of hydrogel strips as described above to which 10× diluted blood, to which 4 of 6 samples were spiked with BK virus. FIG. 8(c) shows the realtime PCR curves and FIG. 8(d) shows the MCA of the 10× diluted blood samples.

Figure 4:
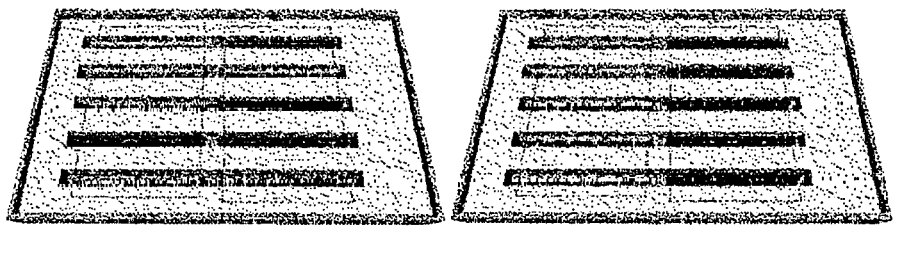
FIG. 4 shows different hydrogel strip arrangements containing multiple primer sets made in one chip.
Figure 5:
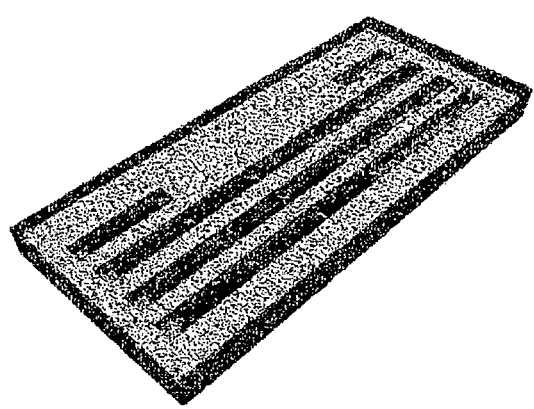
FIG. 5 shows different capillary arrangements.
Figure 5:
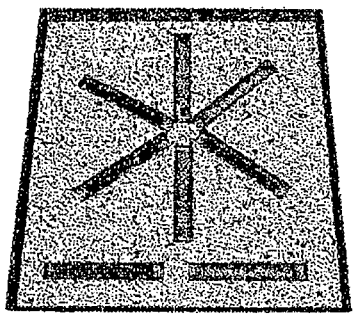
Figure 5:
Figure 5:
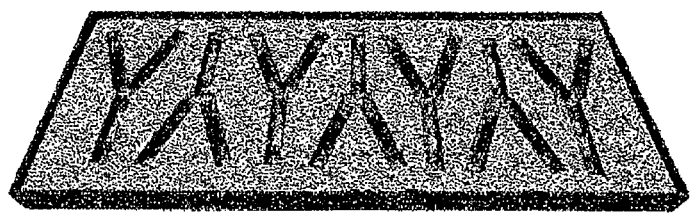

Example 3: Different Configurations of the Chip Containing Hydrogel Capillaries or Hydrogel Strips Hydrogel strips (FIG. 4) or hydrogel capillaries (FIG. 5) can be placed in the wax or plastic chip in different configurations that allow efficient sample delivery as well as multi-patient testing on the same chip. FIG. 4 shows different hydrogel strip arrangements containing multiple primer sets made in one chip, where sample can be delivered to the middle of each channel hydrating both channels on each side of a chip containing 10 different primer sets to detect one patient at a time for multiple diseases (FIG. 4(a)) or a chip containing 2 primer sets detecting several patients at a time (FIG. 4(b)). FIG. 5 illustrates how different capillary arrangements containing different primers may be placed in one chip in order to improve the sample delivery and test multiple patients at a time, wherein sample can be delivered from one end of each lane hydrating all the capillaries (FIG. 5(a)), or sample can be delivered to the middle of the flower arrangement hydrating all the capillaries (FIG. 5(b))

When utilizing wax trenches to receive capillaries, as otherwise disclosed herein, the wax on opposing sides of the trench enclosing the capillary may be indented towards each other using a thin piece of metal or plastic, so as to better hold the capillary and stabilize it against motion during storage or transportation. The metal or plastic may optionally be heated so as to partially melt the wax around the capillary. In the alternative, or in addition to, application of a small amount of trehalose, linear polymer acrylamide or PDMS monomer between the capillary and the supporting surface of wax can assist in the stabilizing of the capillary reaction unit following its polymerization and drying.

Figure 9:
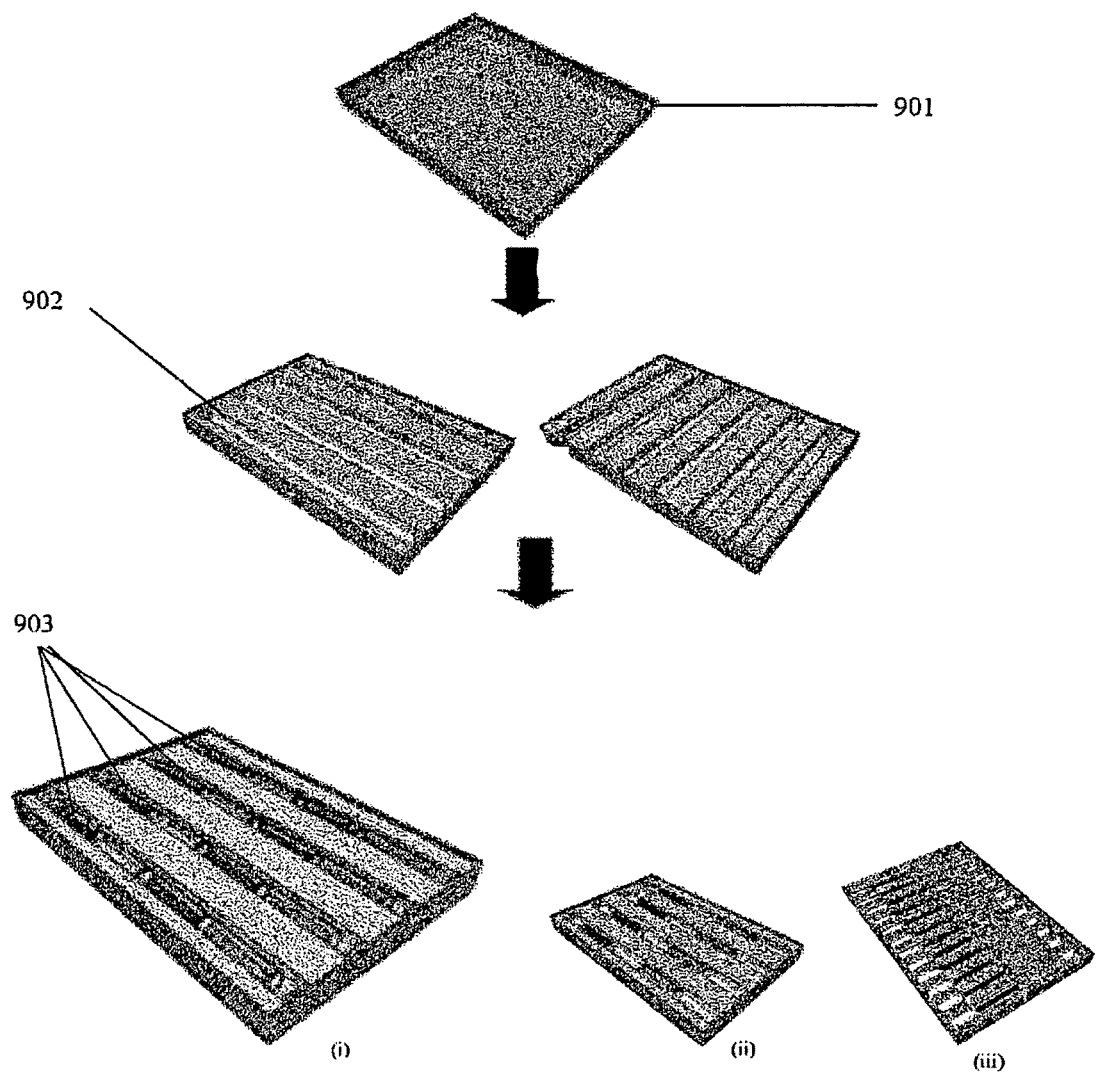
FIG. 9 illustrates the process for manufacturing cassettes of the present invention.

FIG. 9 illustrates the steps for making cassettes of the present invention, with a pan 901 filled with molten wax and trenches 902 imprinted using a stamp, such as a PDMS stamp. Desiccated capillaries, select capillaries labeled as 903, are placed within the wax trenches 902. Different capillary arrangements are possible in the pan; for example, 4 trenches are shown in FIG. 9(i) and FIG. 9(ii). Pans with 6 trenches have also been successfully tested. FIG. 9(i) can have four 6 mm capillaries with 4 different primers in one trench. It is also possible to arrange 6 different capillaries in one trench using 4 mm capillaries (accepting 4 µl of sample) (not shown). Capillaries in the first three trenches accept delivery of samples and one trench is used for the negative control capillaries. Capillaries in trench 4 have DNA template polymerized in the mixture for use as positive controls. A cassette with the arrangement in FIG. 9(i) but with 6 trenches is shown in FIG. 1(b). In FIG. 9(i), the first two capillaries in each trench can have a primer set to detect HSV-1 or HSV-2, respectively, while the 3rd and 4th capillaries in the trench can have primers for detection of *Ureaplasma Urealyticum* (UU) and *Mycoplasma Homonis* (MH) as described in Example 6 herein. The first two capillaries can be spaced such that the sample can be loaded from either side of the cassette to allow delivery of two different sample types, in this example genital swabs and urine.

As an example of an alternate geometry, the cassette in FIG. 9(ii) accepts only two capillaries 7 mm in length, in each trench. The layout for another alternative is a cassette with 10 trenches and two 6 mm long capillaries in each trench (FIG. 9(iii)). Each trench has one capillary to detect HSV-1 and another for HSV-2. The first 9 trenches have capillaries with no DNA while the last trench has capillaries with DNA polymerized in the capillaries as positive controls. This particular cassette can test 8 patients at a time where 8 samples are introduced to the first 8 trenches. The 9$^{th}$ and 10$^{th}$ trenches receive water to hydrate the gels; trench 9 contains the negative control capillaries and trench 10 contains the positive control capillaries.

Figure 10:
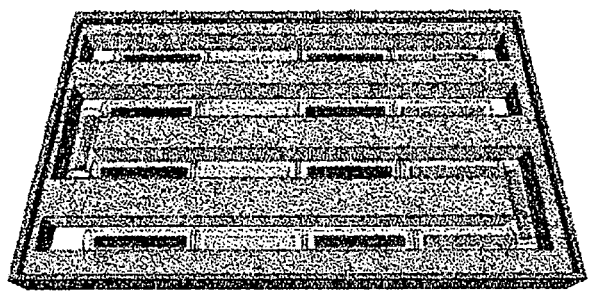
FIG. 10 illustrates delivery of a hydrating sample to multiple lanes of capillaries through a single administration point.
Figure 10:
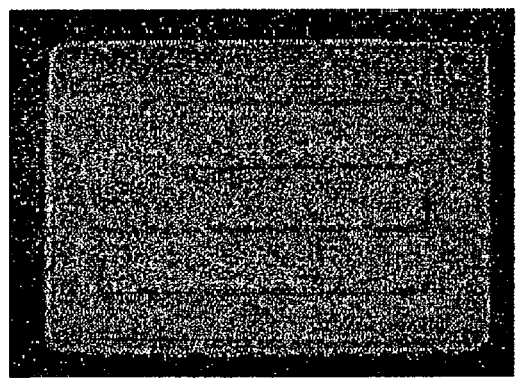
Figure 10:
Figure 10:
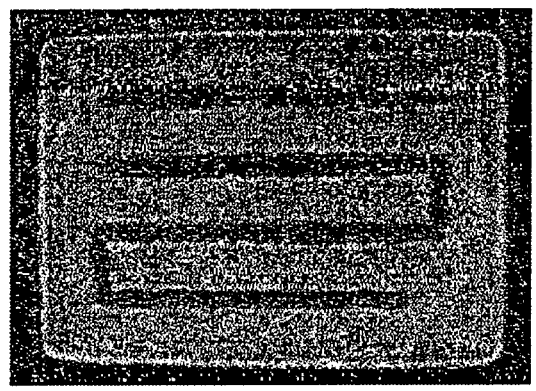

Samples may further be delivered to multiple lanes within a cassette by administration of a hydrating sample to a single port. As shown in FIG. 10 sample may be introduced in the upper left quadrant of the illustrated cassette (FIG. 10(a)), with photos showing before and after administration of hydrating sample communicating throughout the capillaries present within (FIG. 10(b)). The key to consistent fluid communication between the capillaries, is to ensure that there is contact between the ends of capillaries perpendicular to an adjacent capillary and that the aperture for the capillaries be substantially centered with respect to each other.

Example 4: Separating Capillaries to Individual Amplification Chambers

Figure 6:
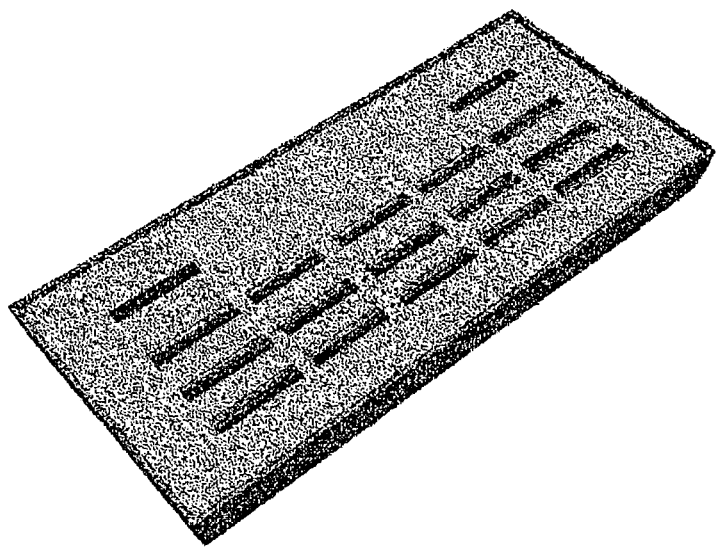
FIG. 6 shows an example of how wax is placed within a chip such that it will flow into the spaces between the capillaries or hydrogel strips, providing separation from the others throughout the PCR or MCA.

Once the wax is melted during the first denaturation step within the PCR process, the fluid wax enters the openings of the hydrogel strips or hydrogel capillaries, thereby separating them into individual reaction chambers and inhibiting cross-contamination between hydrogel strips or hydrogel capillaries which may contain different primers, negative and positive controls, and/or different samples (FIG. 6). Once the analysis is completed, the wax in a chip or cassette containing hydrogel capillaries or hydrogel strips solidifies, thereby containing the hydrogel capillaries or hydrogel hydrogel strips for ease of disposal.

Example 5: Preparation of Glass Capillary Tubes and Placement in Cassette

Glass hemotocrit tubes (Plain, Blue Tip—Fisher Scientific, Fair Lawn, N.J.) were cut to 6 or 7 mm in length. The inner diameter of the capillary is 1.1 mm while the outer diameter is 1.5 mm. Capillaries were heated overnight in an oven at 550° C. to remove any prior coating or treatment. In the presence of these commercial treatments to capillaries, the "noodle" shape of the hydrogel is not properly formed upon desiccation, or alternatively it may spoil or otherwise inhibit the PCR reaction. Therefore, it is vital to remove these coatings or treatments provided in commercially available capillaries.

Figure 11:
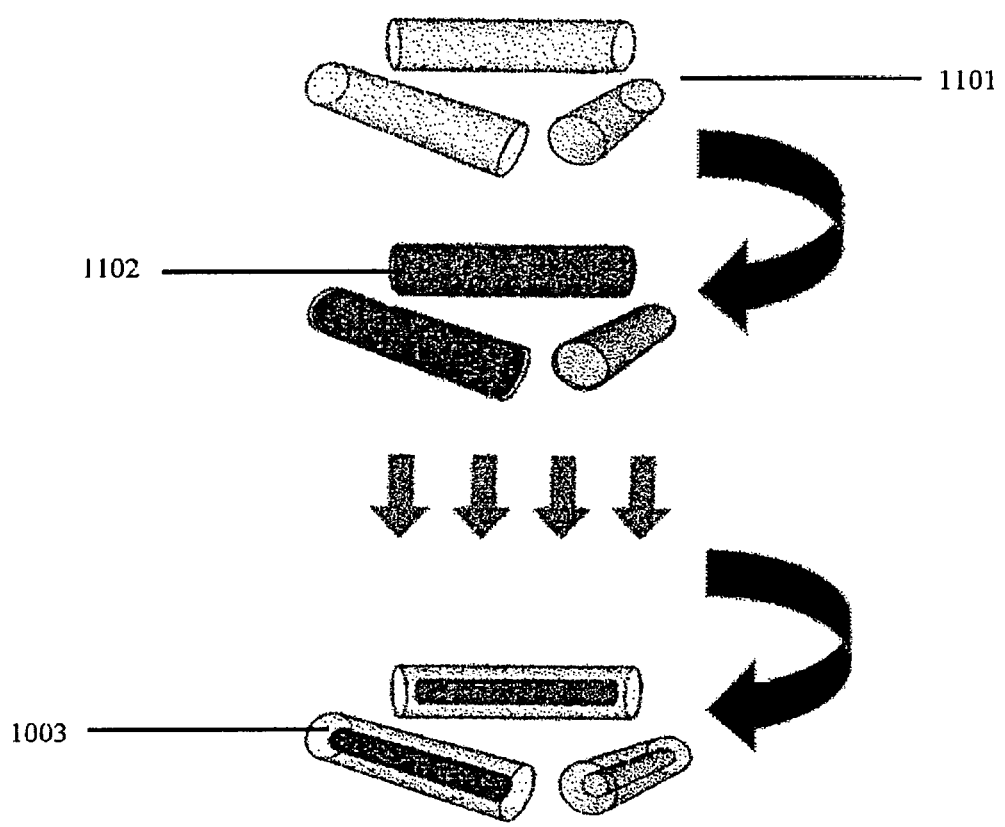
FIG. 11 shows the procedure for making cassettes with capillaries as contemplated by the present invention.

The steps for the preparation of hydrogel capillaries for PCR are shown in FIG. 11. Capillaries 1101 are filled by capillary force with PCR reaction mix and hydrogel reagents 1102, as further described herein. Polymerized hydrogel containing all PCR reagents necessary, save for template, are desiccated forming desiccated hydrogel 1103. Each set of capillaries was filled by dipping one end into the appropriate reaction mix and placed on a cover glass or a petri dish. Capillaries that served as positive controls were filled with the reaction mix containing the specified primer set and a known positive sample (that is, known to contain template nucleic acid) while all the others were filled with reaction mix and the specified primer set but no template. Capillaries were then exposed to 360 nm UV light (~1 mW/cm$^2$ on the capillaries) for 30 min in order to photo-polymerize the hydrogel/reaction mix as 4% acrylamide hydrogel capillaries. They were then desiccated as described below.

The polymerised capillaries were placed in a vacuum oven to desiccate the hydrogel, as is generally known in the art for dehydration of biologically active samples. After desiccation, capillaries hold dried hydrogel in the shape of a "noodle" as shown in FIG. 12(a) for a 7 mm long capillary of 1.1 mm diameter. For delivering the sample to the capillary, the noodle shape of the dried hydrogel is vital as the space created between the hydrogel noodle and the glass capillary walls creates a path for the sample to flow by capillary force and thereby rehydrate the hydrogel. In another embodiment, the size of the noodle after drying is 4.3 mm, but a range of capillary or gel strip sizes are possible.

Paraffin wax (Surgipath Paraplast X-tra, Leica Microsystems) was used to make trenches and to hold reaction units securely in place. To remove background fluorescence, melted wax was filtered at 65° C. through a glass funnel filled with Silica hydrogel 60 (Merck Millipore). One volume of Silica hydrogel filters 4-5 volumes of wax.

An aluminum pan (23.5 mm×32 mm) was used as the base of the cassette to contain wax and capillaries (FIG. 12(b), FIG. 9). A PDMS stamp was made for imprinting trenches in the wax to make a template for laying capillaries in the pan. The pan was filled with about 1.3 mL of molten wax; the PDMS seal was placed on the pan and the wax was allowed to solidify. The stamp was then peeled off to form the cassette with wax trenches; capillaries are then placed in the formed trenches. Different stamps with different geometries can be made depending on the test for which the cassette is intended. The shape of the bottom of each trench is made to the shape of the capillary so that the capillary lies snugly in the wax trench.

A polymer cassette with trenches can also be used to hold capillary reaction units. In the present example, nine parallel trenches 1.6 mm in width with rounded bottoms were milled in a sheet of thermally conductive polymer (Cool Polymers Inc., North Kingstown, R.I., USA) with dimensions of 29 mm×25 mm×3 mm. The thickness of the polymer at the bottom of the trench is 0.4 mm. Each trench was filled with 80 µL of wax prior to arranging the capillaries.

Capillaries can be placed in the pan with different arrangements as shown in FIG. 9(i-iii). Further details of these arrangements are given in Example 3.

Example 6: Demonstration of Nucleic Acid Detection Using Clinical Samples

To demonstrate performance, raw genital swabs and urine were introduced to the same cassette to simultaneously detect four sexually transmitted infections. Herpes Simplex Viruses (HSV-1 and HSV-2) were detected from raw genital swabs. *Ureaplasmd Urealyticum* (UU) and *Mycoplasma Homonis* (MH) were detected from raw urine.

Samples

Genital swab samples (HSV-1 positive, HSV-2 positive, and negative controls—based on testing using culture methods) were obtained from a clinic for sexually transmitted diseases. Genital swabs from patients were placed in universal transport media (UTM; Copan Diagnostics Inc., Murrieta, Calif., USA) at the clinic and transported to the laboratory where they were frozen at −20° C. until use. For all experiments, unprocessed genital swab samples in UTM were used directly without DNA purification. Thirty anonymized urine samples were obtained from the sexually transmitted disease clinic. Unprocessed urine samples were also used without DNA purification.

Reagents

Separate reaction mixes were prepared with (positive controls) or without template for HSV-1, HSV-2, MH, and UU and used to fill capillaries. The primer sets for detecting HSV-1, HSV-2, UU and MH are shown in Table 1. Each 100 pit reaction mix consisted of 20 µL of 5×PCR buffer (333 mM tris-sulfate, pH 8.6, 83 mM $(NH_4)_2SO_4$ (Sigma, St. Louis, Mo.); and 40% sucrose (Sigma)), 30 µL of 40% sugar, 4 µL of 50 mM $MgCl_2$ (Fluka, Buchs), 2 µL of 10 mM [dNTP] (Sigma), 2 µL of 1% BSA (Sigma), 4 µL of 10 µM primer solution (Integrated DNA technologies, San Diego, Calif.) for each of the two primers, 10 µL of 10×LC Green Plus (Idaho Technology Inc., Salt Lake City, Utah) and 4 µL of Taq polymerase (20 units/µL), 10 µL of a 40% acrylamide (Sigma) 4.4% bis-acrylamide aqueous solution (N,N-methylene bisacrylamide, BioRad, Hercules, Calif.), 2 µL of 3% azobis (Wako, Richmond), 1 µL of 10% TEMED (N,N,N',N' tetramethylethylenediamine, Sigma) and water. For the positive controls, 4 µL of sample collected from patients known to be infected was added, replacing water. The mixes were vortexed, centrifuged, and loaded into the capillaries as described below.

TABLE 1

Primers used for amplification of HSV-1, HSV-2, UU and MH targets.

| Primer Name | Sequence (5' to 3') | Identifier |
|---|---|---|
| HSV-1 Forward | GGGCCATTTTACGAGGAGGA | SEQ ID NO 1 |
| HSV-1 Reverse | GGAACGCACCACACAAAAGA | SEQ ID NO 2 |
| HSV-2 Forward | GTTTGGCGTGTGTCTCTGAA | SEQ ID NO 3 |
| HSV-2 Reverse | CTTTTATCCCCGGCACACAG | SEQ ID NO 4 |
| UU Forward | GGAATGACACACGATAAACCCT | SEQ ID NO 5 |
| UU Reverse | TGACAATCGCGCTTCTGTATAA | SEQ ID NO 6 |
| MH Forward | AACGTAGGTTGTACTCCGTAGA | SEQ ID NO 7 |
| MH Reverse | AAGTCGGTTTGCTAACCTCG | SEQ ID NO 8 |

SampleDelivery

The sample is delivered to a single capillary or a line of capillaries that are placed next to each other in the trench by dispensing the sample at one end of the trench such that the sample flows through by capillary forces and rehydrates the gels as shown in FIG. 12(d). The positive and negative control capillaries are rehydrated with water. We used 10× diluted raw genital swab and 10× diluted urine samples with water, both sample types from the ST1 clinic, to rehydrate the hydrogel to test for HSVs, UU and MH for all the experiments. Approximately 20 µL of sample was delivered to a trench with four 6 mm capillaries. The hydrogel takes about 7-8 min to rehydrate.

PCR and Melting Curve Analysis

The instrument used for PCR and MCA is shown in FIG. 12(e) and FIG. 12(f) and a detailed description of the instrument is given in Example 11. Prior to testing on cassettes, conventional PCRs were first performed in order to identify genital swab samples infected with HSV. PCR reaction mix of 25 µL consisted of 5 µL of 5×PCR buffer, 1.5 µL of 50 mM $MgCl_2$, 0.5 µL of 10 mM [dNTP], 0.5 µL of 1% BSA, 0.5 µL of 10 µM each primer, 1 µL HSV sample in UTM, and 0.5 µL of Taq polymerase (20 units/µL). PCRs were performed with a pre-denaturation step of 3 minutes at 94° C., 30 to 40 cycles with 94° C. for 30 s, 60° C. for 30 s, and 72° C. for 30 s, followed by a final extension step of 120 s at 72° C. PCR for determining the primer specificity was also performed with similar reagent and thermal cycling conditions.

The 30 anonymized urine samples were also screened by conventional PCR to identify those with UU and MH infections. The reaction mix is as above except that 2.5 µL of urine was added to the 25 µL reaction mix. Thermocycling conditions were similar to conventional PCR for HSVs.

After the sample was introduced into the cassette, the rehydrated cassette was then placed on the peltier element of the GelCycler for thermal cycling (FIG. 12(e)). After a pre-denaturation step of 3 min at 94° C., 35 cycles of DNA amplification were carried out at 94° C. for 5 s, 60° C. for 10 s, and 72° C. for 10 s, followed by final extension step of 120 s at 72° C. During the PCR, CCD images were taken at 5 s into each extension step. MCA was performed from 70-95° C. and CCD images were taken at every 0.2° C.

For testing on cassettes, the CCD images acquired during PCR and MCA were analyzed to visualize the amplification status and to detect the products in each capillary. Images taken at the extension step of each PCR cycle (35 or 40) were analyzed with ImageJ software (National Institutes of Health, U.S.) using the MicroArray Rectangular Plug-in (Dr. Robert Dougherty, OptiNav Inc., Redmond, Wash.) to plot the cycle number versus the fluorescence intensity in each capillary. Using the software, rectangles were placed around the image of each capillary in the first image, followed by automated analysis of the sequential image series to measure the fluorescence intensity of each capillary during PCR and MCA. The image recognition software acquires this data without human intervention.

Melting curves were created from CCD images taken at 0.2° C. degree interval during the heating of the cassette from 70° C. to 95° C. and were analyzed to measure the melting temperature for amplicons in each capillary, as previously described (Atrazhev, A. et al *Analytical Chemistry*, 2010, 82, 8079; Manage, D. et al *Lab on a Chip*, 2012, 12, 1664). A plot of the negative derivative of this fluorescence with respect to the temperature determines the melting temperature ($T_m$) of the PCR products.

High Sensitivity Detection of HSV in Genital Swabs

Figure 13:
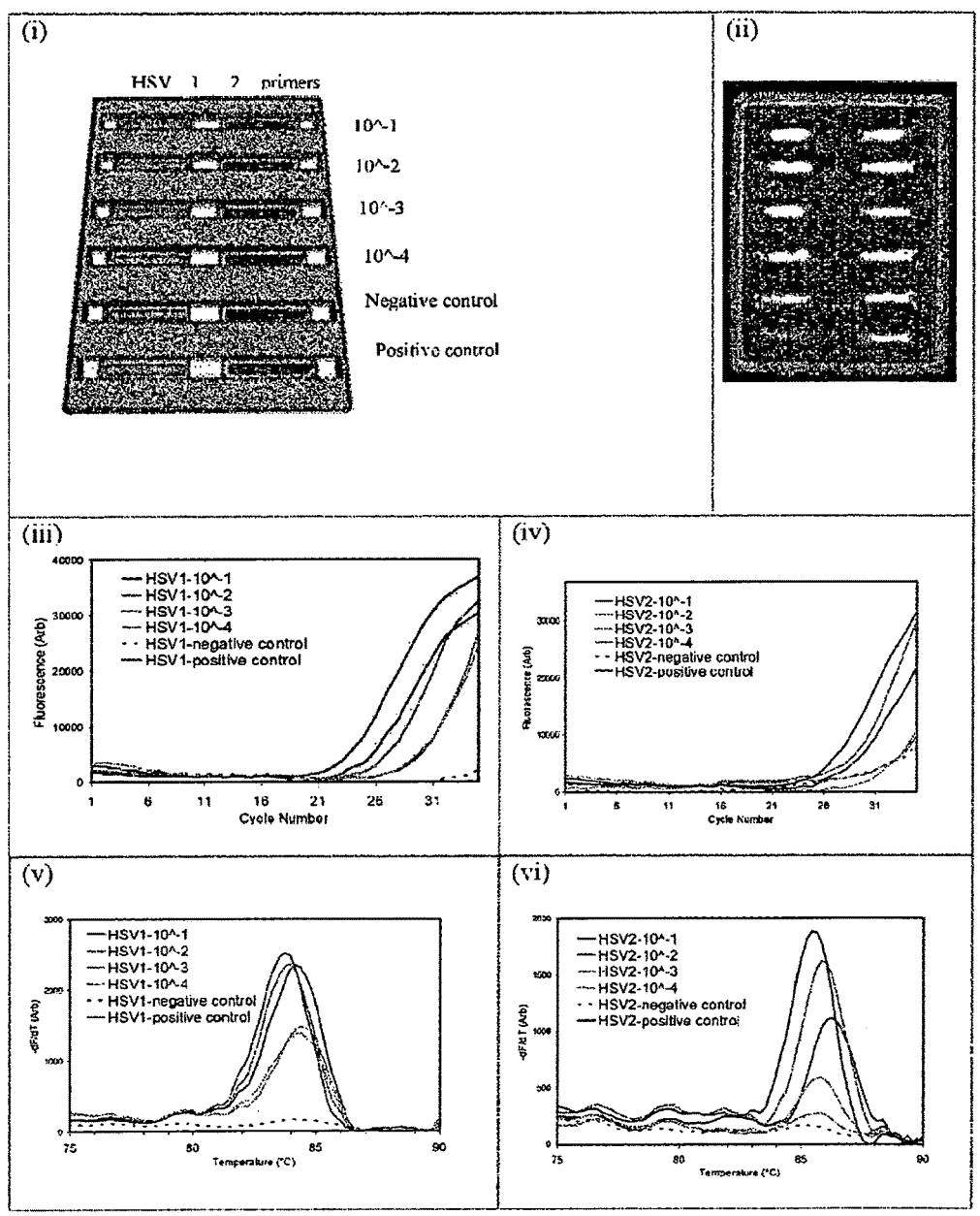
FIG. 13 shows exemplary detection of two STIs in clinical samples.

In order to test the sensitivity of the cassette system, PCR was performed with a dilution series of genital swabs positive for HSV-1 or HSV-2. Serial dilutions of the swab samples were made at dilution factors of $10^{-1}$, $10^{-2}$, $10^{-3}$, and $10^{-4}$ which were then used to hydrate the hydrogel capillaries. The cassette was arranged as shown in FIG. 13(i) and the fluorescence image of the cassette at the 35th PCR cycle is shown in FIG. 13(ii). The PCR data is shown in FIG. 13(iii) and FIG. 13(iv) and MCA data is shown in FIG. 13(v) and FIG. 13(vi) for HSV-1 and HSV-2 respectively, each at different dilutions.

The absolute number of HSV copies from a genital swab is not reported routinely, and is generally not clinically meaningful. FIG. 13 shows that HSV-1 is readily detectable in as little as a 1/10,000 dilution of a genital swab and HSV-2 is weakly detectable in a 1/10,000 dilution. This suggests that very low HSV copy numbers from clinically relevant genital herpes infections are likely to be detectable using this system.

Simultaneous Testing for UU, MH, HSV-1 and HSV-2 on the Same Cassette

HSV-1, HSV-2, UU and MH targets were amplified on the same cassette with genital swabs tested for HSVs and urine samples tested for *mycoplasma* targets (UV and MH). The capillary arrangement for a four target STI panel is shown in FIG. 14(i). These data show the capability of the cassette for detecting multiple infections in multiple sample types from one or more patients. It further confirms that amplification occurs independently in each capillary with no cross contamination along the trench.

Figure 14:
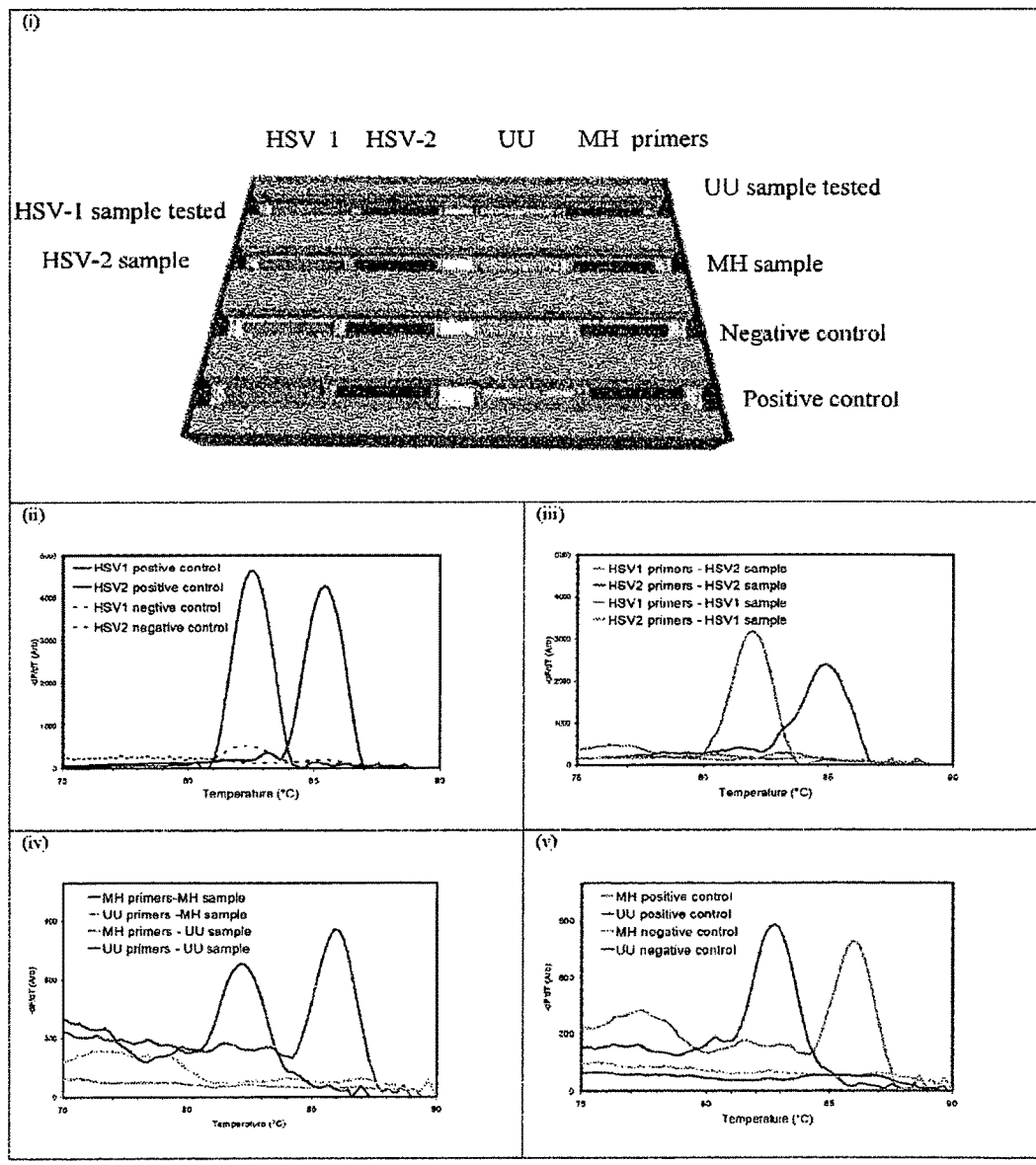
FIG. 14 shows exemplary simultaneous detection of 4 STIs in two different types of clinical sample.

FIG. 14 shows the simultaneous detection of 4 STIs in two different types of clinical sample (genital swabs and urine). FIG. 14(i) shows the capillary arrangement for and sample types delivered to a wax cassette to detect HSV-1 and HSV-2 from genital swabs on the same cassette with UU and MH from urine. FIG. 14(ii) shows MCA data from the positive and negative controls for HSV-1 and HSV-2, FIG. 14(iii) the MCA data for HSV-1 and HSV-2 sample detection, FIG. 14(iv) the positive and negative controls for UU and MH, and FIG. 14(v) UU and MH sample detection. The melt temperatures of UU and MH specific PCR amplified fragments are 82° C. and 86° C. respectively.

Example 7: Demonstration of Long-Term Stability of Cassettes

Capillaries are readily filled with hydrogel mixture and are flexible in terms of using different primer sets in assembled cassettes, with no cross-contamination as shown above and in later sections. However, for use in a clinical setting, pre-made cassettes should have a prolonged shelf life, with unprocessed samples introduced at the time of testing. The use of freshly polymerized gels is incompatible with these requirements as sample cannot be added to a capillary after polymerization. After filling capillaries with hydrogel reaction mixture, the hydrogel inside the capillaries was desiccated. Desiccated hydrogel accounts for about ~15-18% of the whole capillary volume and holds a shape of a noodle inside the gel thereby creating a channel, which is essential for delivery of the sample to the capillary which rehydrates the hydrogel at the time of testing.

In order to study the stability of the reagents at room temperature for long term storage, separate sets of stored cassettes were then tested after 1 week, 1.5 months, and 3 months.

Figure 15:
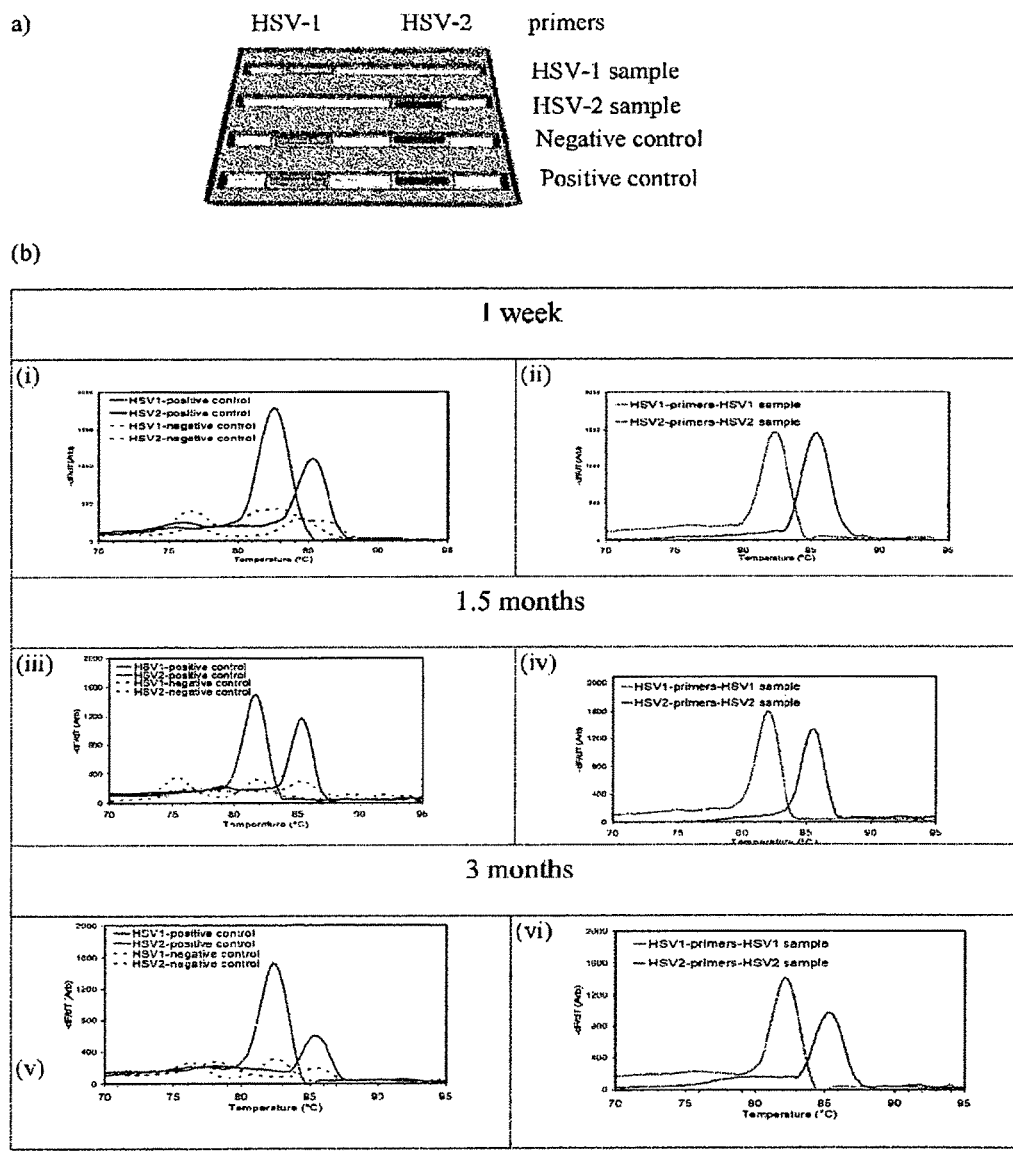
FIG. 15 illustrates the effects of storage of vacuum-sealed desiccated hydrogel cassettes.

A set of experiments was designed to confirm that PCR reagents in desiccated capillary reaction units could still support PCR and were stable at room temperature for at least 3 months. As shown in FIG. 15, cassettes contained desiccated capillary units for detecting HSV-1 and HSV-2 as well as negative and positive controls. FIG. 15(a) shows the capillary arrangement, with capillaries in the first two trenches testing samples for HSV-1 and HSV-2 while the third and fourth trenches contain negative and positive control capillaries. The first and second trenches were rehydrated with HSV-1 and HSV-2 samples, respectively, while the third and fourth trenches were rehydrated with water. FIG. 15(b) shows MCA data after storage for one week (FIG. 15(b)(i), FIG. 15(b)(ii)), 1.5 months (FIG. 15(b)(iii), FIG. 15(b)(iv)), and 3 months (FIG. 15(b)(v), FIG. 15(b)(vi)). Real time quantitative PCR $C_p$ values after one week, 1.5 month, and 3 months are 23.2, 23.5, and 21.4 for HSV-1 sample; 27.2, 26.5, and, 26.0 for HSV-2 sample; 21.4, 20.3, and 19.8 for HSV-1 positive control; and 27.6, 27.3, and 27.2 for HSV-2 positive control respectively showing that for stored reaction units were comparable for all time points, indicating equivalent amplification capabilities over the time. Cassettes were also successfully stored at 4° C. and −20° C.

MCA data from FIG. 15 shows that the reagents within the cassette maintain activity for at least three months of storage at room temperature. $C_p$ values were equivalent to controls for all time points (FIG. 15), indicating comparable amplification. This suggests that cassettes holding gel-filled capillaries are feasible for detecting pathogens in resource-limited areas of the world where refrigeration and power are erratic or unavailable.

Based upon these observations, cassettes were pre-made and stored in vacuum-sealed bags at room temperature for at least several days before use. Air-tight sealing during storage was essential to prevent any further loss of moisture that can compromise enzyme activity. The wax pan with desiccated hydrogel capillaries placed in the trenches in different arrangements was stored in a vacuum-sealed bag as shown in FIG. 12(c). A commercially available food vacuum sealer was used to seal the packages.

Example 8: Absence of Cross Contamination in Cassette PCR

Capillaries with desiccated hydrogel noodles each containing a primer set for a different pathogen can be arranged in wax trenches such that the sample can be delivered from one end to the all of the capillaries in a given trench as shown in FIG. 12(d). These cassettes can be manufactured to perform multiparameter PCR with different testing panels for simultaneous detection of multiple pathogens. However, it was critical to confirm that the different primers or amplicons from adjacent capillaries do not cross-contaminate each other.

Cassettes having 4 trenches with four 6 mm capillaries per trench were arranged with alternate HSV-1 and HSV-2 capillaries physically adjacent to each other within the trench along which sample flows. This is shown in FIG. 16(i) where the first two trenches receive samples, and trenches 3 and 4 receive water for the negative and positive controls. Samples were from patients with known HSV status.

Figure 16:
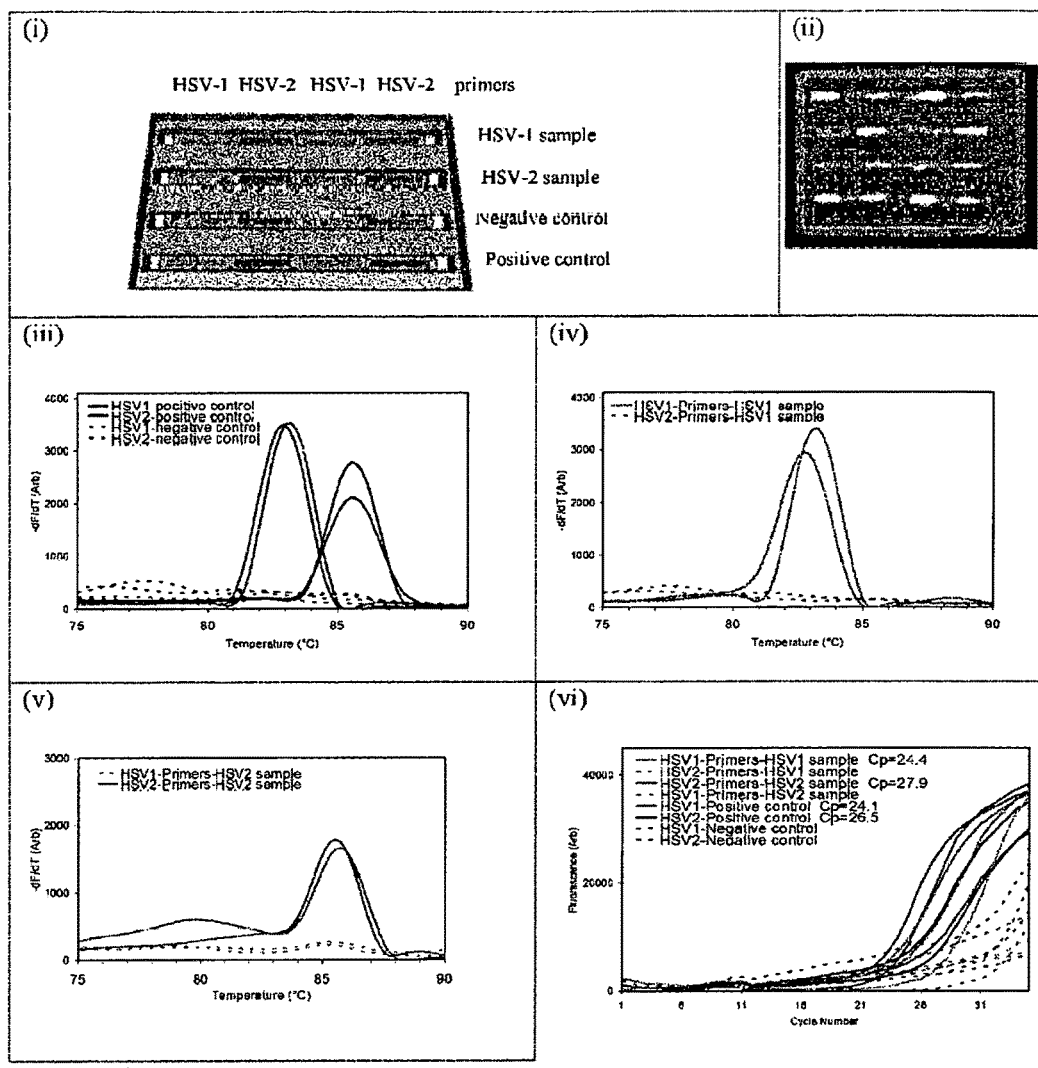
FIG. 16 shows the absence of cross-contamination between capillaries with different primers contained within.

Experiments to evaluate cross contamination are shown in FIG. 16. FIG. 16(iii-v) shows that each capillary produces only the correct product; the capillary with HSV-1 primers only amplifies HSV-1 positive samples but not HSV-2 positive samples and vice versa, regardless of the reaction specificity of neighboring capillaries in the trench. This can be seen in the CCD image shown in FIG. 16(ii). These results show that the primers or amplicons in adjacent capillaries do not travel or diffuse outside their own boundaries and hence no cross contamination is detectable during the sample delivery or during the rehydration process. We observed that as PCR begins, the wax melts and the openings of each capillary are sealed instantly thereby preventing any communication between the capillaries during the PCR and MCA.

FIG. 16(i) shows the capillary layout and the sample delivery information for a cassette with 4 trenches where each trench contains HSV-1 and HSV-2 test capillaries alternately placed. HSV-1 and HSV-2 samples were tested in trenches 1 and 2, respectively, while trench 3 is a negative control and trench 4 is the positive control. FIG. 16(ii) shows a CCD image at the 35$^{th}$ cycle of PCR, MCA curves: (iii) positive and negative controls—trenches 3 and 4, (iv) HSV-1 sample delivery to trench 1, and (v) HSV-2 sample delivery to trench 2. PCR products were also sequenced to confirm their identities. Real-time PCR data for each capillary is shown in FIG. 16(vi).

These results also confirm primer specificity and highlight the importance of MCA for the correct interpretation of fluorescence data. The amplified products from the hydrogel were extracted from capillaries and sequenced to confirm their identity. Any primer-dimers or incorrect amplification will contribute to overall fluorescence and hence influence the amplification curve, giving an incorrect $C_p$ value. For this reason, MCA is essential to confirm product identity by observing a defined melt peak at the correct $T_m$ for the expected amplicon.

Example 9: Multi-Target Screening of Samples from Multiple Patients

Figure 17:
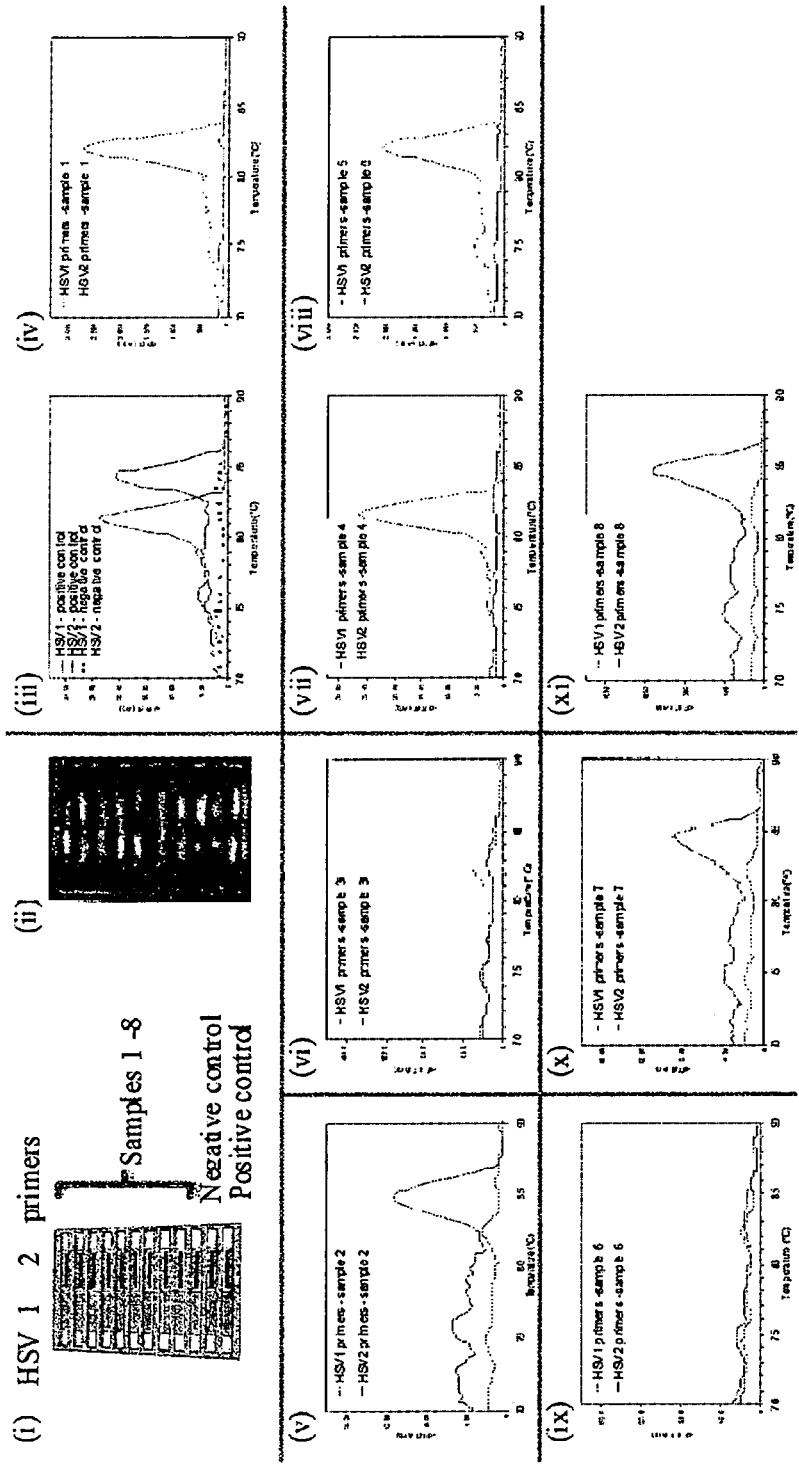
FIG. 17 shows exemplary simultaneous detection of STIs in samples from different patient samples on a single cassette.

A cassette with capillaries arranged in an aluminium pan to simultaneously detect 2 STIs in multiple patients (HSV-1 and HSV-2) is shown in FIG. 17. The capillaries are 6 mm in length.

The CCD image at 30th cycle of PCR is shown in FIG. 17(i). The MCA data for negative and positive controls are shown in FIG. 17(iii) while the data for 8 different samples are shown in FIG. 17(iv-xi), with one sample applied per trench. This experiment further confirms that the capillaries do not communicate or contaminate each other during sample delivery, the rehydration process or during the PCR and MCA.

Figure 18:
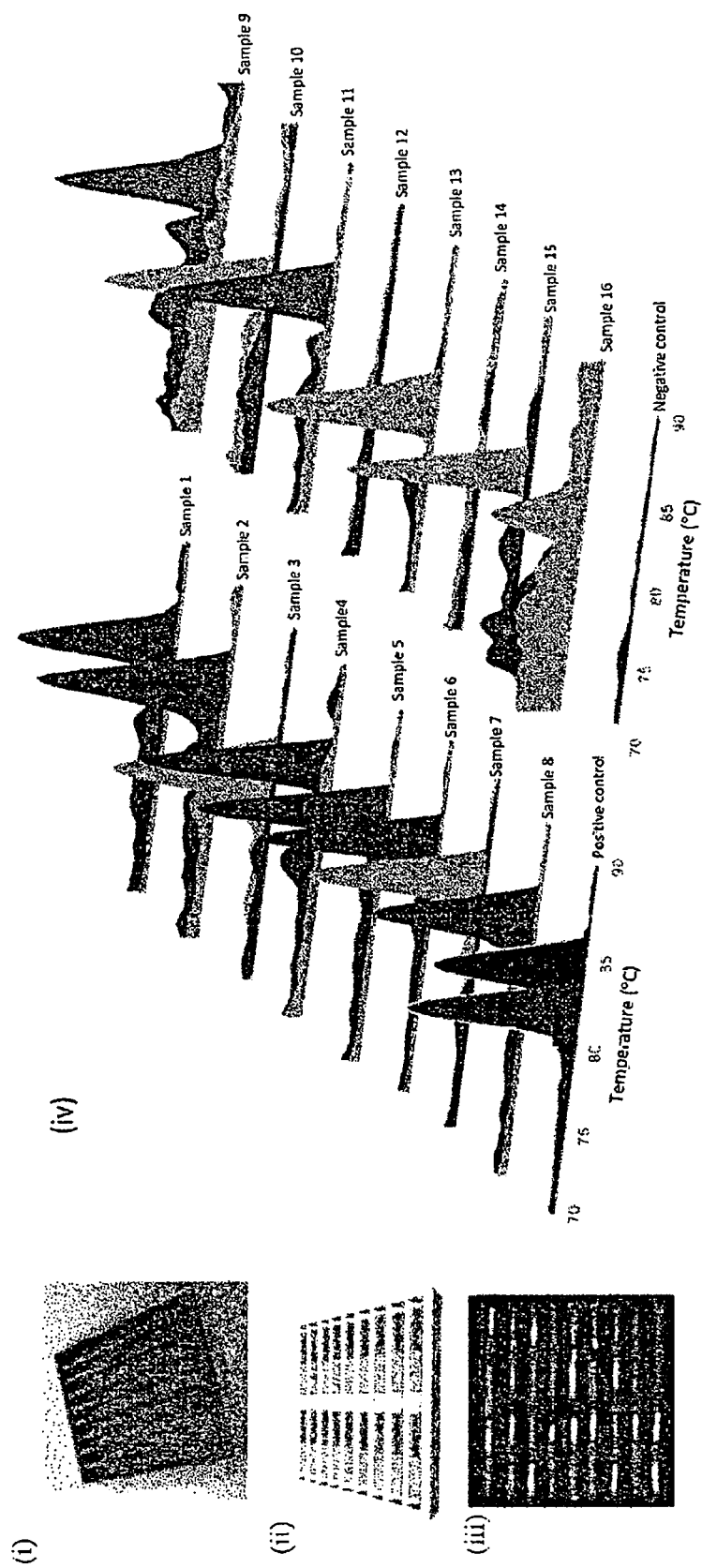
FIG. 18 shows exemplary simultaneous detection of 16 patient samples using a polymer cassette.

A cassette with a black polymer pan is capable of testing 16 HSV raw genital swab samples is shown in FIG. 18(i) and FIG. 18(ii) respectively. The use of black polymer prevents fluorescence bleed that can otherwise occur when capillaries are too closely proximate. During thermal cycling the wax in the polymer trenches melts and capillaries sink to the bottom of the trench, providing for improved thermal contact with the pan. MCA results in FIG. 18(iv) show results from a large number of samples in adjacent trenches, with two different samples per trench simultaneously tested for two STIs, in the same cassette. There is no detectable cross-contamination despite the close proximity of samples and reaction units.

FIG. 18(iii) shows a CCD image at the 35$^{th}$ cycle of PCR, and (iv) MCA curves for all 16 samples and positive and negative controls (HSV-1 and HSV-2 are red and blue respectively). All 16 samples were accurately identified including two negative samples (#12, #14).

Example 10: Genomic DNA Amplification in Hydrogel Capillaries

The device and system described herein, in particular in Example 6, was used to perform amplification of DNA obtained from buccal swabs of humans to detect two Single Nucleotide Polymorphisms (SNPs), rs1219648 and rs2981582, with allele specific PCR. The primers utilized are shown in Table 2. The buccal swab was dissolved in a commercial pre-treatment solution by moving it in the solution for about 10 s, the swab was then removed, and was heated at two different temperatures for total of 8 min according to the manufacturer's instructions. It was then diluted 10× and added to the capillaries.

TABLE 2

Primers used for amplification of rs1219648 and rs2981582 SNPs from human genome.

| Primer Name | Sequence (5' to 3') | Identifier |
| --- | --- | --- |
| rs1219648-Wildtype Reverse (rs121-WT) | CATGGCCATCCTTGAAGACT | SEQ ID NO 9 |
| rs1219648-Mutant Reverse (rs121-MT) | CATGGCCATCCTTGAAGACC | SEQ ID NO 10 |
| rs1219648-common Forward (rs121-F) | ATGGCGCAGAATTACTTACA | SEQ ID NO 11 |
| rs2981582-Wildtype Forward (rs298-WT-F) | ATCGCCACTTAATGAACCTGTTTCC | SEQ ID NO 12 |
| rs2981582-Wildtype Reverse (rs298-WT-R) | CTCCTTCCTAAACTGTCCTGA | SEQ ID NO 13 |
| rs2981582-Mutant Forward (rs298-MT-F) | CGCCACTTAATGAACCTGTTTCT | SEQ ID NO 14 |
| rs2981582-Mutant Reverse (rs298-MT-R) | TCCTTCCTAAACTGTCCTGA | SEQ ID NO 15 |

Shown in FIG. 17 and FIG. 18 is the simultaneous detection of STIs in samples from 8 different patient samples on the same cassette. FIG. 17(i) shows the capillary layout with the first 8 trenches detecting 8 samples while the 9$^{th}$ trench is a negative control and the 10$^{th}$ trench is the positive control. FIG. 17(ii) shows a CCD image at 30th cycle of PCR. FIG. 17(iii) shows the MCA of the positive and negative controls, with the MCA profile shown in FIG. 17(iv) that of sample 1 (HSV-1), FIG. 17(v) sample 2 (HSV-2), FIG. 17(vi) sample 3 (Negative), FIG. 17(vii) sample 4 (HSV-1), FIG. 17(viii) sample 5 (HSV-1), FIG. 17(ix) sample 6 (Negative), FIG. 17(x) sample 7 (HSV-2), and FIG. 17(xi) sample 8 (HSV-2). FIG. 18 shows the simultaneous testing for STIs of 16 patient samples using a polymer cassette. Specifically FIG. 18(i) shows a photograph of the polymer pan with trenches, FIG. 18(ii) the capillary layout. The first 8 trenches accept 16 different samples while the 9th trench contains positive and negative controls, the left and right shadings representing the capillaries containing HSV-1 and HSV-2 primers respectively.

Figure 19:
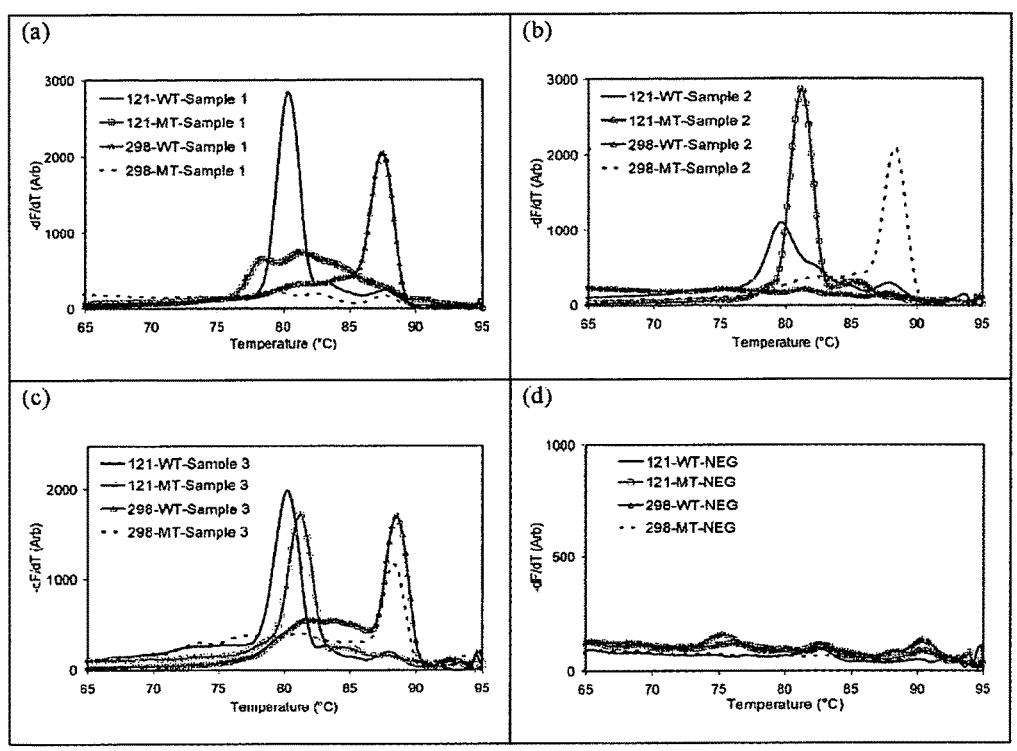
FIG. 19 shows detection of SNPs from human genomic DNA obtained from buccal swabs.
Figure 20:
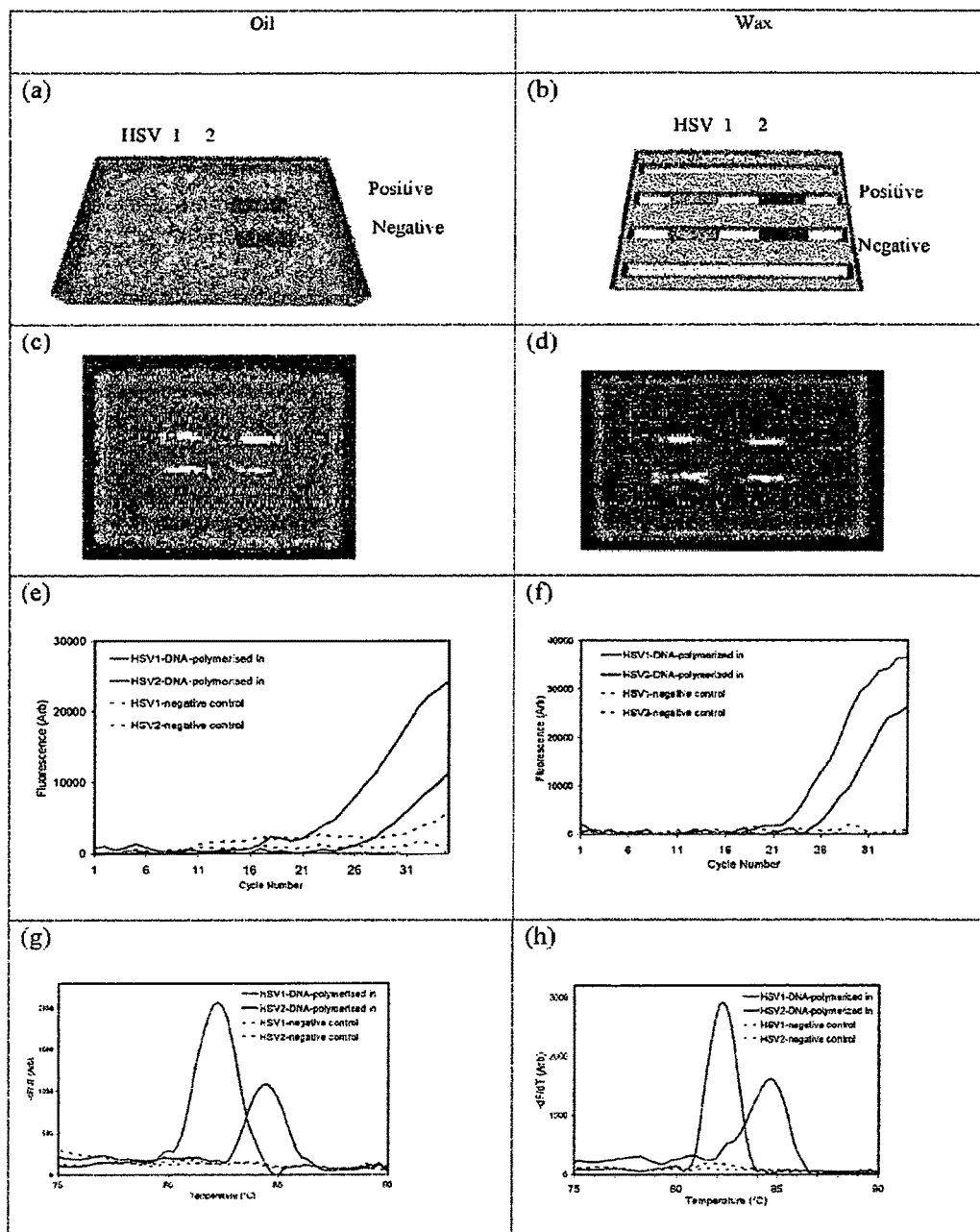
FIG. 20 shows a comparison of oil and wax as vapour barriers.

As shown in FIG. 19(a) wildtype sample is only amplified by rs121-wiltype (WT) and rs298-WT primers, but not with rs121-mutant(MT) and rs298-MT primers. FIG. 19(b) shows that homozygous sample is only amplified by rs121-MT and rs298-MT primers but not with rs121-WT and rs298-WT primers; while FIG. 19(c) shows that the heterozygous mutant sample is amplified by all 4 sets of primers and FIG. 19(d) shows the negative controls.

Figure 12:
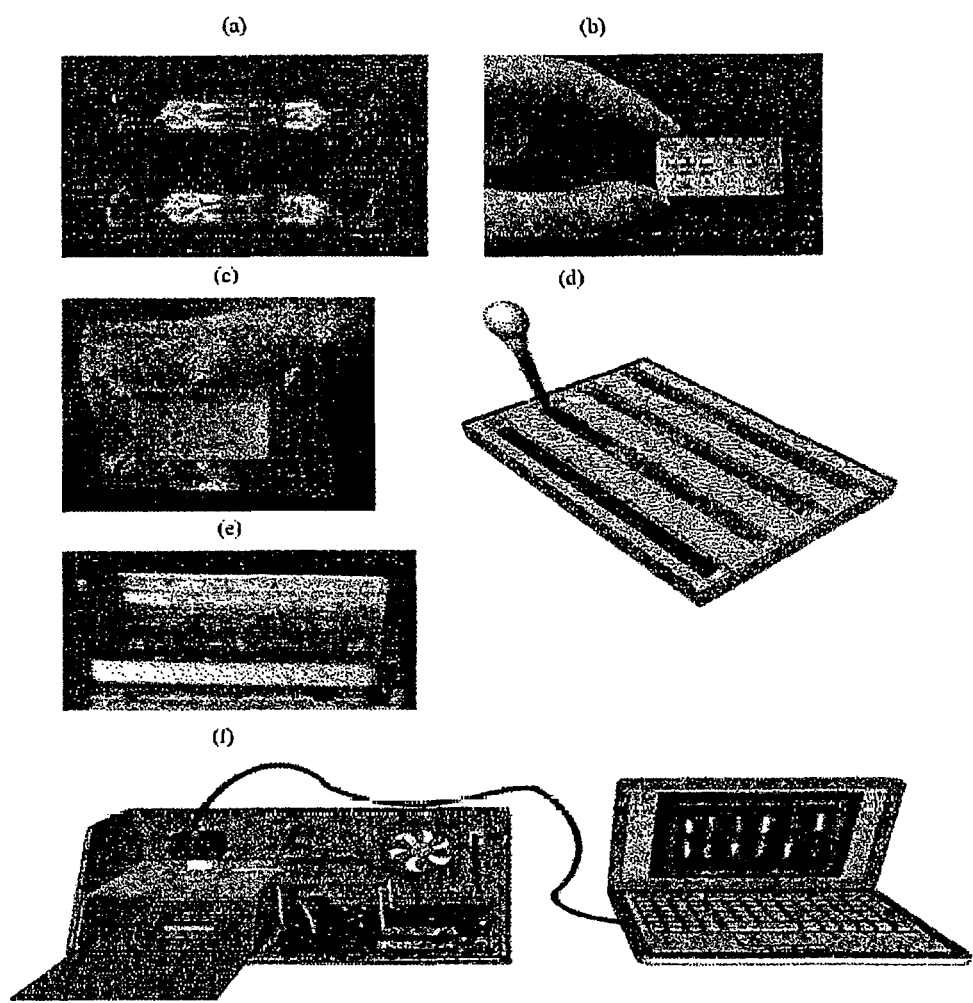
FIG. 12 shows an overview of the cassettes and system of the present invention.

Example 11: Instrument and System for Receiving Cassettes and Performing PCR and MCA FIG. 12 shows an overview of the presented system. FIG. 12(a) shows a dried hydrogel inside capillary reaction units, while FIG. 12(b) shows a cassette with capillaries arranged in 6 trenches. FIG. 12(c) shows a vacuum packaged cassette, as described herein. FIG. 12(d) shows an example of sample delivery with a transfer pipette to each trench of the cassette from one end of the trench. The sample flows smoothly through the entire trench and hydrates hydrogel in the capillaries. FIG. 12(e) shows a cassette with a 4 trench capillary arrangement in melted wax during thermal cycling.

In order to perform PCR and MCA in a pan with hydrogel capillaries, the prototype instrument shown in FIG. 12(f) was used. This instrument incorporates off the shelf components to measure the fluorescence from hydrogel capillaries for real time PCR and MCA, collecting images with a CCD camera (Point Grey Research) and a 445 nm laser (Ultralasers Inc) for excitation of the LCGreen dye. A ring illuminator (Dolen Jenner) diffuses the laser light onto the pan for even illumination. It uses a Peltier element for heating and cooling during the thermocycling. The Peltier element, CCD camera and the laser are controlled by a microprocessor. A 12.5 mm lens made by Fujinon is used to focus the fluorescence light onto the CCD camera. A 30 nm wide band-pass interference filter centred at 530 nm (Chroma Technology) is placed in front of the camera. A laptop computer running a customized Java-based program is used to control the instrument. The user enters the PCR and MCA parameters as well as the camera parameters. During the PCR, at the extension phase of each cycle, the laser switches on and an image of illuminated capillaries is captured, to collect the information for real time PCR analysis. During MCA, the laser is continuously switched on and images are acquired at 0.2° C. intervals with the temperature increment set at 0.1° C./s. The system is calibrated with a K-type thermocouple (Omega Engineering Inc.) placed inside a gel-filled capillary.

Example 12: Comparison of Oil and Wax as a Vapour Barrier

A comparison of oil and wax as vapour barriers for gel-filled capillaries was performed using HSV-1 or HSV-2 in raw genital swabs and amplified on cassettes in wax or covered in mineral oil. Template DNA was polymerized into the hydrogel along with the other reagents, using freshly filled and polymerized hydrogel in capillaries. The DNA in these capillaries was polymerized into the hydrogel while the negative controls lacked DNA template. Real-time PCR data and MCA data are shown in FIG. 20. FIG. 20(*a*) shows the capillary arrangement in the pan in oil and FIG. 20(*b*) in wax. FIG. 20(*e*) shows CCD images at the $35^{th}$ cycle of PCR in oil and with FIG. 20(*d*) showing the same in wax. Real-time PCR data was collected for all 4 capillaries in oil and in wax as shown in FIG. 20(*d*) and FIG. 20(*f*) respectively; with MCA data of all 4 capillaries in oil and in wax shown in FIG. 20(*g*) and FIG. 20(*h*) respectively. The melting temperatures of HSV-1 and HSV-2 are 82±0.7° C. and 85±0.6° C., respectively. This demonstrates that using oil and wax as vapour barriers, are very similar and that both media provide a suitable vapour barrier to keep the gels hydrated during thermal cycling and MCA.

While particular embodiments of the present invention have been described in the foregoing, it is to be understood that other embodiments are possible within the scope of the invention and are intended to be included herein. It will be clear to any person skilled in the art that modifications of and adjustments to this invention, not shown, are possible without departing from the spirit of the invention as demonstrated through the exemplary embodiments. The invention is therefore to be considered limited solely by the scope of the appended claims.

What is claimed is:

1. A cassette for performing interrogations for the presence of a nucleic acid within an aqueous sample comprising
    a pan containing within it solid wax with at least one trench on its surface;
    a multiplicity of capillaries with two opposing apertures; wherein
        said capillaries contain a desiccated hydrogel containing all components needed for a cell-free nucleic acid amplification other than the template nucleic acid,
        within the capillaries there exists a path described by the inner diameter of said capillary and said desiccated hydrogel which allows atmospheric communication between opposing apertures and through said capillaries,
        said capillaries are within said trench with the longitudinal axis of said capillary parallel to the longitudinal axis of said trench,
        said trench resists the motion of said capillaries through friction between the inner longitudinal surface of said trench and the longitudinal surface of said capillaries with at least one end of said capillary is capable of receiving an aqueous sample,
        said wax is optically transparent to at least two wavelengths of electromagnetic radiation wherein said at least two wavelengths are capable of differentiation by an optical detector, and
        said pan is capable of containing the wax when in a molten state.

2. The cassette of claim 1 wherein the wax is Paraffin wax.

3. The cassette of claim 1 wherein said capillaries are less than 2 mm in diameter.

4. The cassette of claim 3 wherein said capillaries have an inner diameter of 1.1 mm.

5. The cassette of claim 1 wherein said pan is thermally conductive.

6. The cassette of claim 5 wherein said pan is aluminum.

7. The cassette of claim 1 wherein said pan absorbs electromagnetic radiation of at least one of said at least two wavelengths.

8. The cassette of claim 1 wherein said desiccated hydrogel is polymerized acrylamide and bis-acrylamide.

9. The cassette of claim 8 wherein said desiccated hydrogel is 4% acrylamide and 0.4% bis-acrylamide.

10. The cassette of claim 1 wherein said components needed for a cell free nucleic acid amplification system comprises the enzymes, substrates and primers needed for a polymerase chain reaction.

11. The cassette of claim 10 wherein said components needed for a cell free nucleic acid amplifications system comprises tris-sulfate, $(NH_4)_2SO_4$, $MgCl_2$, all four deoxyribonucleotides, Bovine Serum Albumin, at least two primers designed to hybridize with a target nucleotide sequence, a heat stable DNA polymerase, azobis, TEMED and water.

12. The cassette of claim 11 wherein said components needed for a cell free nucleic acid amplifications system includes LC Green.

13. A system for detecting the presence of a nucleic acid within an aqueous sample comprising
    a pan containing within it solid wax with at least one trench on its surface;
    a multiplicity of capillaries with two opposing apertures;
    means for controlling temperature in thermal communication with said pan;
    illumination source; and
    optical detector,
    wherein
        The amplification of a nucleic acid is detected through an increase in an optical signal received by said optical detector resulting from the interaction of an illumination wavelength provided by said illumination source, said capillaries contain a desiccated hydrogel containing all components needed for a cell-free nucleic acid amplification other than the template nucleic acid, within the capillaries there exists a path described by the inner diameter of said capillary and said desiccated hydrogel which allows atmospheric communication between opposing apertures and through said capillaries;

said capillaries are within said trench with the longitudinal axis of said capillary parallel to the longitudinal axis of said trench, said trench resists the motion of said capillaries through friction between the inner longitudinal surface of said trench and the outer longitudinal surface of said capillaries with at least one end of said capillary is capable of receiving an aqueous sample, said wax is optically transparent to at least two wavelengths of electromagnetic radiation provided by said illumination source wherein said at least two wavelengths are capable of differentiation by an optical detector, and said pan is capable of containing the wax when in a molten state.

14. The system of claim 13 wherein the wax is Paraffin wax.

15. The system of claim 13 wherein said capillaries are less than 2 min in diameter.

16. The system of claim 15 wherein said capillaries have an inner diameter of 1.1 mm.

17. The system of claim 13 wherein said pan is thermally conductive.

18. The system of claim 17 wherein said pan is aluminum.

19. The system of claim 13 wherein said pan absorbs electromagnetic radiation of at least one of said at least two wavelengths.

20. The system of claim 13 wherein said desiccated hydrogel is polymerized acrylamide and bis-acrylamide.

21. The system of claim 20 wherein said desiccated hydrogel is 4% acrylamide and 0.4% bis-acrylamide.

22. The system of claim 13 wherein said components needed for a cell free nucleic acid amplification system comprises the enzymes, substrates and primers needed for a polymerase chain reaction.

23. The system of claim 22 wherein said components needed for a cell free nucleic acid amplifications system comprises tris-sulfate, $(NH_4)_2SO_4$, $MgCl_2$, all four deoxyribonucleotides, Bovine Serum Albumin, at least two primers designed to hybridize with a target nucleotide sequence, a heat stable DNA polymerase, azobis, TEMED and water.

24. The system of claim 23 wherein said components needed for a cell free nucleic acid amplifications system includes LC Green.

25. The system of claim 24 wherein said illumination means is a laser emitting light at a wavelength of 445 nm.

26. The system of claim 13 where said optical detection means is a CCD camera with a band-pass interference filter centered at 530 nm.

27. A cassette for performing interrogations for the presence of a nucleic acid within an aqueous sample comprising
a pan containing within it solid wax with at least one trench on its surface;
a multiplicity of capillaries with two opposing apertures; wherein
said capillaries contain a desiccated hydrogel containing all components needed for a cell-free nucleic acid amplification other than the template nucleic acid,
within the capillaries there exists a path described by the inner diameter of said capillary and said desiccated hydrogel which allows atmospheric communication between opposing apertures and through said capillaries;
said capillaries are within said trench with the longitudinal axis of said capillary parallel to the longitudinal axis of said trench, and
said trench resists the motion of said capillaries through friction between the inner longitudinal surface of said trench and the longitudinal surface of said capillaries with at least one end of said capillary is capable of receiving an aqueous sample.

* * * * *